US 8,157,816 B2

(12) United States Patent
Rotella et al.

(10) Patent No.: US 8,157,816 B2
(45) Date of Patent: Apr. 17, 2012

(54) GASTROPEXY KIT

(75) Inventors: John Anthony Rotella, Roswell, GA (US); Donald Jay McMichael, Roswell, GA (US); Nathan Christopher Griffith, Roswell, GA (US); Thomas Gregory Estes, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 768 days.

(21) Appl. No.: 11/848,534

(22) Filed: Aug. 31, 2007

(65) Prior Publication Data
US 2009/0062743 A1   Mar. 5, 2009

(51) Int. Cl.
*A61B 17/10* (2006.01)
(52) U.S. Cl. .................. 606/139; 606/232; 24/132 R
(58) Field of Classification Search .............. 24/132 R; 112/302, 254, 222, 223; 206/63.3, 439; 600/37; 128/898, 899; 604/174, 175, 170.07; 606/108, 606/139, 144, 148, 151, 153, 156, 157, 213, 606/216, 217, 221, 232, 233, 154
See application file for complete search history.

(56) References Cited

U.S. PATENT DOCUMENTS

| | | | |
|---|---|---|---|
| 1,673,486 A * | 6/1928 | Berge | 470/3 |
| 2,075,508 A | 3/1937 | Davidson | |
| 3,664,345 A | 5/1972 | Dabbs et al. | |
| 4,249,535 A | 2/1981 | Hargest, III | |
| 4,291,698 A | 9/1981 | Fuchs et al. | |
| 4,315,513 A | 2/1982 | Nawash et al. | |
| 4,393,873 A | 7/1983 | Nawash et al. | |
| 4,666,433 A | 5/1987 | Parks | |
| 4,685,901 A | 8/1987 | Parks | |
| 4,701,163 A | 10/1987 | Parks | |
| 4,705,040 A * | 11/1987 | Mueller et al. | 606/108 |
| 4,798,592 A | 1/1989 | Parks | |
| 4,823,794 A | 4/1989 | Pierce | |
| 4,852,568 A | 8/1989 | Kensey | |
| 4,890,612 A | 1/1990 | Kensey | |
| 5,019,093 A | 5/1991 | Kaplan et al. | |
| 5,037,429 A | 8/1991 | Hermes et al. | |
| 5,041,129 A | 8/1991 | Hayhurst et al. | |
| 5,049,138 A | 9/1991 | Chevalier et al. | |

(Continued)

FOREIGN PATENT DOCUMENTS
EP   1159919 A2   12/2001
(Continued)

OTHER PUBLICATIONS

English Abstract for EP 1159919, Dec. 5, 2001, Derwent WPI.

*Primary Examiner* — Ryan Severson
*Assistant Examiner* — David Eastwood
(74) *Attorney, Agent, or Firm* — Karl V. Sidor; Sue C. Watson

(57) ABSTRACT

A gastropexy kit includes a plurality of safety needle assemblies. Each safety needle assembly includes a needle and a stylus. A fastener is positioned in a distal end of the needle. The fastener is coupled to one end of the suture and a suture retention hub is coupled to an opposite end of the suture. The fastener is deployed in a patient's stomach via the needle and stylus which has a blunt distal end which extends through the needle to push the fastener out of the needle and to blunt the needle. The suture retention hub is positioned on a patient's skin and adjustably tensions the suture, which, desirably, is a resorbable suture.

18 Claims, 25 Drawing Sheets

U.S. PATENT DOCUMENTS

| | | |
|---|---|---|
| 5,051,272 A | 9/1991 | Hermes et al. |
| 5,053,047 A | 10/1991 | Yoon |
| 5,061,274 A | 10/1991 | Kensey |
| 5,074,846 A | 12/1991 | Clegg et al. |
| 5,112,310 A | 5/1992 | Grobe |
| 5,121,836 A | 6/1992 | Brown et al. |
| 5,123,912 A | 6/1992 | Kaplan et al. |
| 5,123,914 A | 6/1992 | Cope |
| 5,129,511 A | 7/1992 | Brown et al. |
| RE34,021 E | 8/1992 | Mueller et al. |
| 5,154,283 A | 10/1992 | Brown |
| 5,167,627 A | 12/1992 | Clegg et al. |
| 5,192,302 A | 3/1993 | Kensey et al. |
| 5,222,976 A | 6/1993 | Yoon |
| 5,222,978 A | 6/1993 | Kaplan et al. |
| 5,226,912 A | 7/1993 | Kaplan et al. |
| 5,246,104 A | 9/1993 | Brown et al. |
| 5,249,582 A * | 10/1993 | Taylor .................. 600/567 |
| 5,258,015 A | 11/1993 | Li et al. |
| 5,261,210 A | 11/1993 | Brown |
| 5,261,886 A | 11/1993 | Chesterfield et al. |
| 5,269,809 A | 12/1993 | Hayhurst et al. |
| 5,273,529 A | 12/1993 | Idowu |
| 5,306,289 A | 4/1994 | Kaplan et al. |
| 5,307,924 A * | 5/1994 | Manosalva et al. ......... 206/63.3 |
| 5,312,345 A * | 5/1994 | Cole ..................... 604/110 |
| 5,312,435 A | 5/1994 | Nash et al. |
| 5,316,013 A * | 5/1994 | Striebel et al. ............. 600/567 |
| 5,318,543 A * | 6/1994 | Ross et al. ............. 604/170.01 |
| 5,330,503 A | 7/1994 | Yoon |
| 5,341,823 A | 8/1994 | Manosalva et al. |
| 5,359,831 A | 11/1994 | Brown et al. |
| 5,366,081 A | 11/1994 | Kaplan et al. |
| RE34,866 E | 2/1995 | Kensey et al. |
| 5,391,159 A | 2/1995 | Hirsch et al. |
| 5,417,036 A | 5/1995 | Brown |
| 5,425,445 A | 6/1995 | Brown et al. |
| 5,447,966 A | 9/1995 | Hermes et al. |
| 5,451,212 A | 9/1995 | Andersen |
| 5,456,697 A | 10/1995 | Chesterfield et al. |
| 5,462,162 A | 10/1995 | Kaplan et al. |
| 5,468,252 A | 11/1995 | Kaplan et al. |
| 5,531,699 A * | 7/1996 | Tomba et al. ............ 604/170.02 |
| 5,531,759 A | 7/1996 | Kensey et al. |
| 5,531,761 A | 7/1996 | Yoon |
| 5,545,178 A | 8/1996 | Kensey et al. |
| 5,626,614 A | 5/1997 | Hart |
| 5,702,352 A | 12/1997 | Kimura et al. |
| 5,743,882 A * | 4/1998 | Luther .................. 604/164.05 |
| 5,849,019 A * | 12/1998 | Yoon .................... 606/157 |
| 5,851,195 A | 12/1998 | Gill |
| 6,030,364 A | 2/2000 | Durgin et al. |
| 6,039,714 A | 3/2000 | Cracauer et al. |
| 6,063,106 A | 5/2000 | Gibson |
| 6,077,250 A | 6/2000 | Snow et al. |
| 6,090,073 A | 7/2000 | Gill |
| 6,106,499 A * | 8/2000 | Overton et al. .......... 604/170.01 |
| 6,110,183 A | 8/2000 | Cope |
| 6,186,985 B1 | 2/2001 | Snow |
| 6,260,699 B1 | 7/2001 | Kaplan et al. |
| 6,293,961 B2 | 9/2001 | Schwartz et al. |
| 6,315,789 B1 | 11/2001 | Cragg |
| 6,319,271 B1 | 11/2001 | Schwartz et al. |
| 6,328,720 B1 | 12/2001 | McNally et al. |
| 6,332,877 B1 | 12/2001 | Michels |
| 6,402,722 B1 | 6/2002 | Snow et al. |
| 6,432,123 B2 | 8/2002 | Schwartz et al. |
| 6,582,443 B2 | 6/2003 | Cabak |
| 6,626,919 B1 | 9/2003 | Swanstrom |
| 6,629,957 B1 * | 10/2003 | Wiklund ................. 604/192 |
| 6,669,707 B1 | 12/2003 | Swanstrom et al. |
| 6,673,058 B2 | 1/2004 | Snow |
| 6,699,263 B2 | 3/2004 | Cope |
| 6,773,440 B2 | 8/2004 | Gannoe et al. |
| 6,896,665 B2 | 5/2005 | Picha et al. |
| 6,902,541 B2 | 6/2005 | McNally et al. |
| 6,966,916 B2 | 11/2005 | Kumar |
| 6,997,931 B2 | 2/2006 | Sauer et al. |
| 7,033,380 B2 | 4/2006 | Schwartz et al. |
| 7,066,944 B2 | 6/2006 | Laufer et al. |
| 7,582,098 B2 * | 9/2009 | Gobel .................... 606/153 |
| 2004/0034369 A1 | 2/2004 | Sauer et al. |
| 2004/0153103 A1 | 8/2004 | Schwartz et al. |
| 2004/0226145 A1 * | 11/2004 | Ouellette et al. ......... 24/113 MP |
| 2004/0267209 A1 * | 12/2004 | Kunishige ............... 604/243 |
| 2005/0004540 A1 | 1/2005 | McNally et al. |
| 2005/0020988 A1 * | 1/2005 | Woehr et al. ............. 604/243 |
| 2005/0143691 A1 | 6/2005 | Picha et al. |
| 2005/0149120 A1 | 7/2005 | Collier et al. |
| 2005/0149121 A1 * | 7/2005 | Crombie et al. .......... 606/232 |
| 2005/0165419 A1 | 7/2005 | Sauer et al. |
| 2005/0203550 A1 | 9/2005 | Laufer et al. |
| 2006/0095008 A1 | 5/2006 | Lampropoulos et al. |
| 2006/0100643 A1 | 5/2006 | Laufer et al. |
| 2006/0135996 A1 | 6/2006 | Schwartz et al. |

FOREIGN PATENT DOCUMENTS

| | | |
|---|---|---|
| EP | 1749481 A1 | 2/2007 |
| WO | WO 95/03837 | 2/1995 |
| WO | WO 98/26821 | 6/1998 |
| WO | WO 02/066108 | 8/2002 |
| WO | WO 2006/111394 | 10/2006 |

* cited by examiner

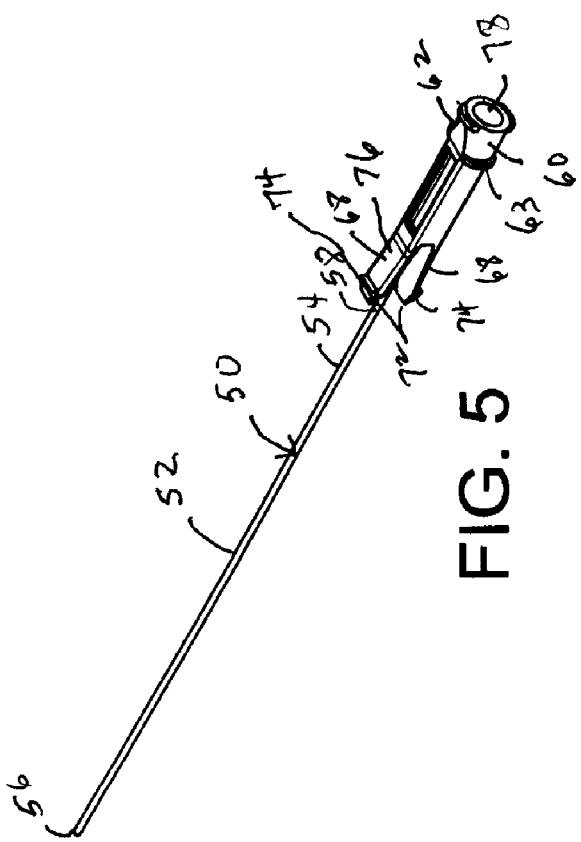

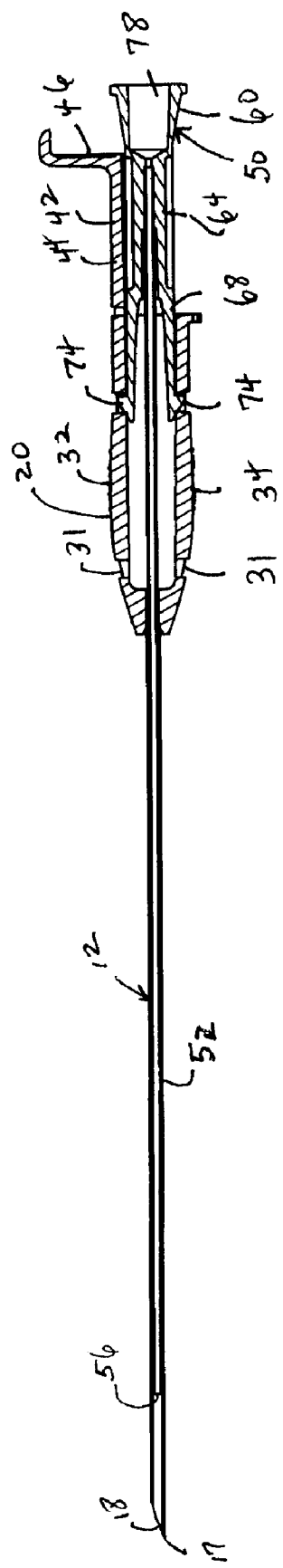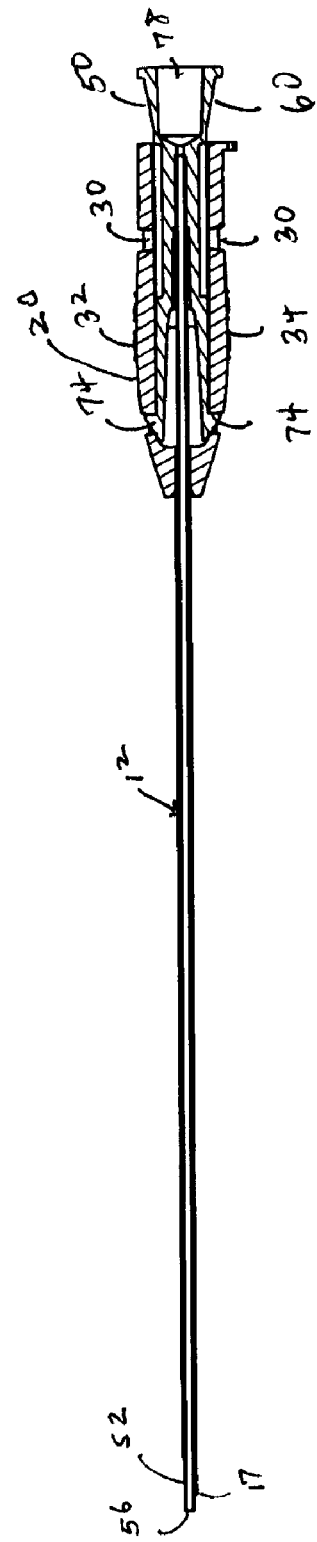
FIG. 15
FIG. 16

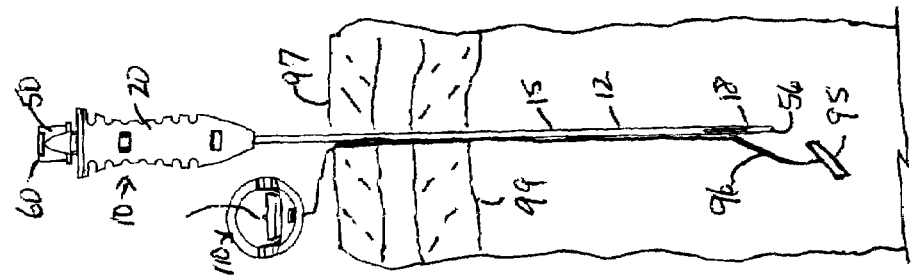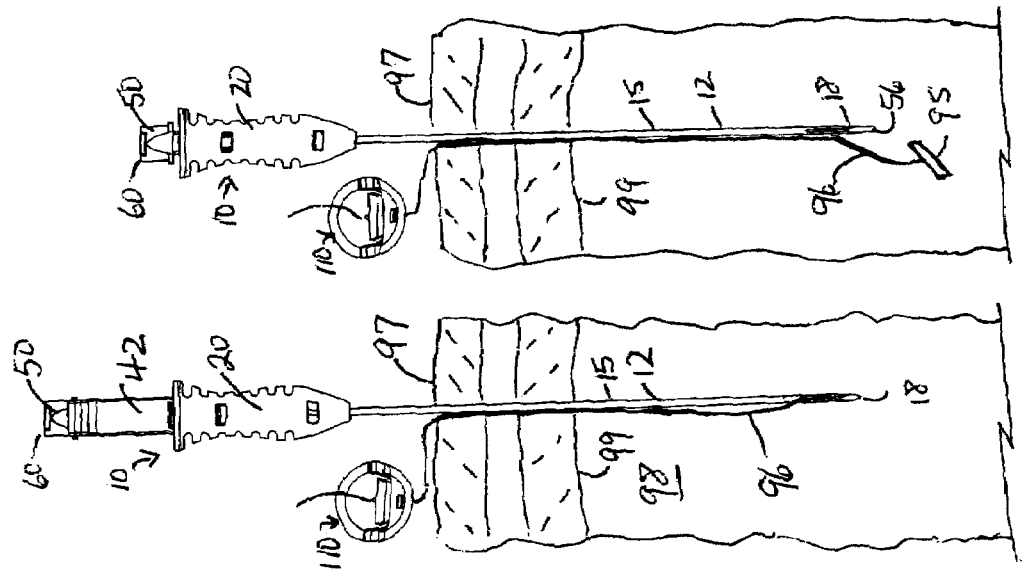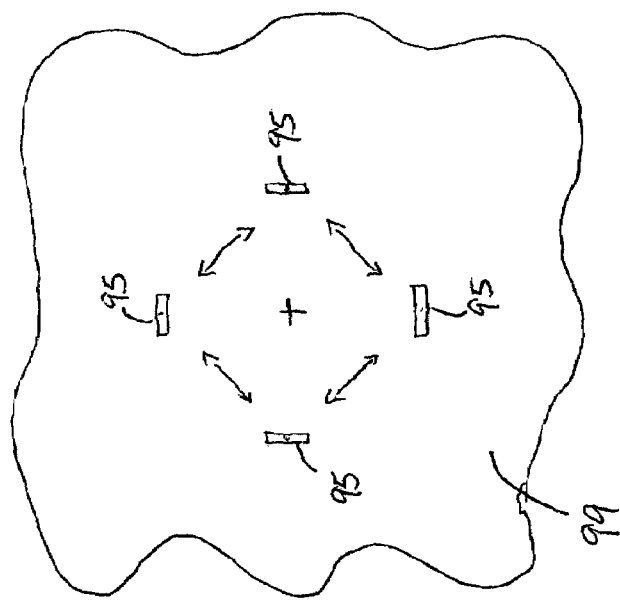

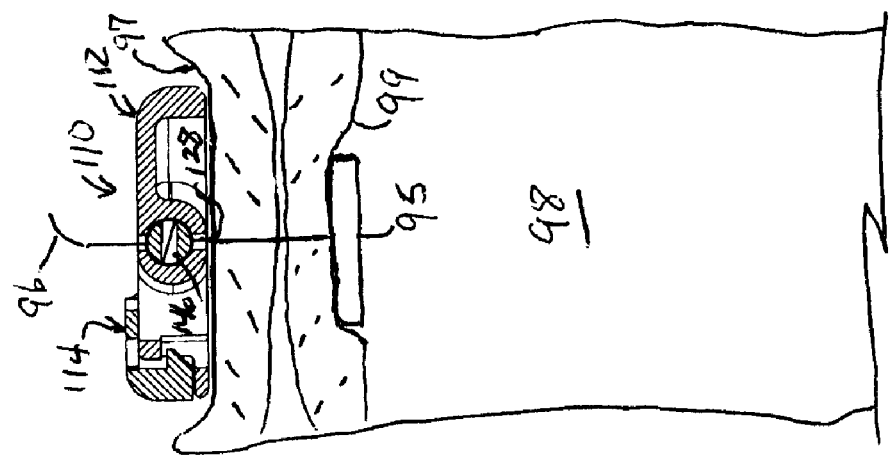
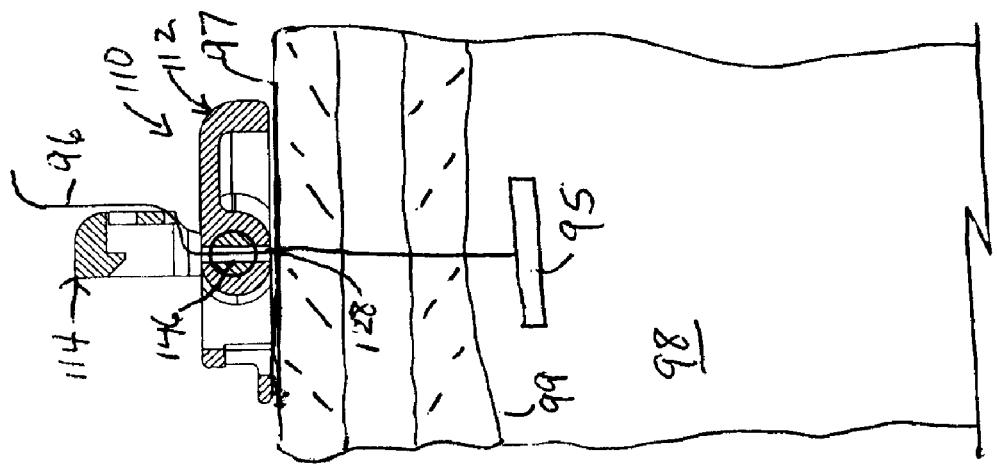

GASTROPEXY KIT

BACKGROUND OF THE INVENTION

This invention relates to a gastropexy kit having at least one hollow needle configured to hold a fastener. The fastener is held in a shaft of a needle. The fastener desirably has a suture coupled thereto and, near an opposite end, a suture holder, for use in a percutaneous fixation of a patient's stomach.

Health care providers are at risk of exposure to blood-borne pathogens, including, for example, hepatitis B, hepatitis C, HIV, and the like. The risk of an accidental stick from a sharp object, such as a needle, exists in many medical procedures. One such procedure is gastropexy, in which a needle is used to pierce a patient's abdominal wall to place one or more fasteners in a patient's stomach. Such a needle must be sharp, so that it penetrates through the patent's skin and abdominal wall to the stomach. A fastener, such as a "T-bar" fastener, carried at or near the tip of the needle is desirably deployed by the needle so that it can be positioned against an inner wall of the stomach. A tensioning suture is connected to the fastener and, at an opposite end of the suture on the outer surface of the patient's body, the suture is desirably also connected to a suture holder, which permits adjustment of the tension on the suture. In this manner, when the suture is tensioned a patient's stomach wall is more closely positioned to the outer surface of the patient's body, and the stomach is stabilized in a position. Usually, at least three and desirably four fasteners are placed in a triangular, square, or diamond-shaped configuration through a patient's skin and into the stomach. Gastropexy is used to isolate and stabilize a portion of a patient's stomach, so that a tissue opening or stoma may be created in the middle of the triangular, square or diamond configuration of fasteners and suture holders, to permit placement of a feeding tube, and so forth.

After each fastener is positioned by a needle, the needle still remains as a sharp hazard, in its position inside of the patient's stomach, as well as when it is removed therefrom. Therefore, there is a need to provide an apparatus which permits blunting of the needle after the fastener is deployed from the needle. Desirably, the needle may be blunted while it is still in a position in the patient's stomach. Further, it is desirable that a health care provider easily detect whether the needle has been blunted once a safety apparatus has been activated. Once activated, the blunting safety apparatus desirably may not be deactivated, so that the needle could not be rendered a sharp hazard again. Finally, such a blunting safety apparatus is desirably activated by a single-handed technique, i.e., the hand holding a proximal end of the needle, thereby allowing the health care provider's hands to remain away from a sharp distal end of the needle during such activation of a safety blunting apparatus.

It is also desirably to provide a method and apparatus so that the plurality of fasteners deployed in a patient's stomach do not need to be removed via an invasive method after gastropexy. As noted, during a gastropexy procedure, it is desirable to place three or four fasteners against a patient's stomach wall. Once a stoma is created, it is desirable to keep the fasteners, suture and suture holder in a position for two to three weeks, so that the stoma becomes well stabilized, and so that gastric liquids, and so forth, do not contaminate and cause infection in a patient's peritoneal cavity. Removing the fasteners after the requisite stabilization time, however, can be problematic.

Sometimes a needle apparatus is used to follow the suture back through a patient's skin to attempt to percutaneously retrieve each fastener. Such a procedure causes new trauma, with new risks of infection. Alternatively, laproscopic methods are used to retrieve each fastener. Such a procedure often involves anesthesia, and again may cause trauma in a patient's mouth, esophagus, and/or stomach.

It would be desirably to use a resorbable suture with the fastener. Such a resorbable suture would crimp or otherwise couple to the fastener at one end, and desirably, a suture holder at an opposite end. The suture would be absorbed by the patient's body after the critical two to three week period. Therefore, no invasive procedure would be required to remove the fasteners. The fasteners would fall away from a wall of the stomach, and follow a patient's digestive tract to be expelled.

The suture holder on a patient's skin is also part of the gastropexy procedure. In some instances, a suture holder is not used, and the opposite end of the suture, which extends to the patient's skin, is temporarily stitched to the patient's skin. In other procedures, the external opposite end of the suture is clamped via an external retention device that usually includes a cotton ball, a plastic washer, plastic tubing, and one or more metal crimps. There are problems with both of these external suture retention methods.

Patients dislike having external stitches, which can pull against the skin, or catch on clothing or gowns. Further, additional suturing requires additional skill and safety risks for the physician. Moreover, after external sutures are in place, there may be confusion as to why the sutures are present. There is a risk that a health care provider, as a result of this confusion, will try to cut and pull out the external suture(s). Issues also exist with retention devices.

One retention device, described above, has many drawbacks. It cannot easily be cleaned. That is, the cotton ball, which is positioned against the patient's skin, may easily harbor bacteria and microorganisms, and may be difficult to change. Further, the device uses plastic tubing, washers, and metal crimps. The combination of components in this retention device results in a high profile away from the skin, typically 0.75 inches or more. These devices may pull, catch on clothing, or rub against the skin, causing abrasion or necrosis due to pressure.

There exists a need for a suture retention hub that has a low profile against a patient's skin. Such a device would be easily recognizable to health care provider as a retention hub for anchoring an internally disposed device via a suture. The hub would desirably by formed from a material which has excellent biocompatibility and ease of cleaning. Such a material would desirably be soft and provide cushioning against a patient's skin, to prevent abrasion and/or necrosis. Such a hub would permit an adequate retention force, and desirably would permit easy tensioning of the suture by a simple manipulation of the hub.

Definitions

As used herein, the term "stylus" refers to a solid or hollow rod which has a blunted, non-sharp distal end, which is sized to fit and move within and extend through at least a sharp end of a hollow needle. The stylus is desirably, but not by way of limitation, made from the same material as the sharp end of the needle. However, the stylus may be made from any material(s) so long as it operates as shown and/or described herein.

As used herein, the terms "comprise", "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "has" and/or "have", and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the terms "resilient", "resilience" and/or "resiliency" and any derivatives thereof refers to the physical property of an object and/or a material that can return to its original form, shape and/or position after deformation such as being bent, compressed, or stretched that does not exceed its elastic limit.

As used herein, the term "couple" includes, but is not limited to, joining, connecting, fastening, linking, or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line or in parallel lines.

As used herein, the terms "orientation" or "position" used interchangeably herein refer to the spatial property of a place where or way in which something is situated; for example, "the position of the hands on the clock."

As used herein, the term "about" refers to an amount that is plus or minus ten (10) percent of a stated number or a stated or implied range.

These terms may be defined with additional language in the remaining portions of the specification.

SUMMARY OF THE INVENTION

In response to the difficulties and problems discussed herein, a gastropexy kit is provided. The kit comprises a plurality of safety needle assemblies. Each safety needle assembly comprises a needle including a shaft having a sharp open distal end with a slot therein and an open proximal end. The proximal end has a needle hub thereon. The needle hub has an opening therethrough which is continuous with an opening provided through the shaft of the needle. The needle hub includes at least one recess. The needle assembly also includes a stylus. The stylus has a shaft including a blunt distal end and a proximal end having a stylus hub thereon. The hub of the stylus includes a retainer. The needle assembly also includes a fastener having a suture coupled thereto. The fastener is positioned in the distal end of the needle with the suture extending through the slot. The stylus is held in a first position when the stylus is positioned inside of the needle, and the blunt distal end of the stylus extends a distance toward the open distal end of the needle but is retained within the shaft of the needle by a portion of the retainer held in one recess in the needle hub. When the hub of the stylus is pushed to move the blunt distal end of the stylus within the shaft of the needle, the stylus moves within the shaft and contacts the fastener therein thereby ejecting the fastener from the shaft. The blunt distal end extends beyond the sharp distal end of the needle and the portion of the retainer is positioned in another recess in the needle hub, thereby rendering the safety needle assembly in a blunted condition, the stylus configured to non-releasably couple to the needle to provide an unmovable position of the stylus with respect to the needle to maintain the blunted condition. The gastropexy kit also includes a suture retention hub coupled to a portion of each suture. The suture retention hub comprises a first base including an upper surface. The suture retention hub also includes a second base moveably coupled to the first base, at least one of the first base and the second base formed to include at least one aperture therethough. When the second base is positioned substantially at a 90 degree angle relative to the upper surface of the first base, the suture positioned through the aperture is moveable through the hub. When the second base is positioned substantially parallel to the upper surface of the first base, the suture positioned through the aperture is not moveable through the hub.

In another aspect of the invention, a gastropexy kit is provided. The kit includes a plurality of safety needle assemblies. Each safety needle assembly comprises a needle including a shaft having a sharp open distal end having a slot therein and an open proximal end. The proximal end has a needle hub thereon. The needle hub has an opening therethrough which is continuous with an opening provided through the shaft of the needle. The needle hub includes at least one movable stop positioned thereon. The needle hub also includes at least one recess therein. The safety needle assembly also includes a stylus. The stylus has a shaft including a blunt distal end and a proximal end having a stylus hub thereon. The hub includes an edge and a retainer. The safety needle assembly also includes a fastener having a suture coupled thereto. The fastener is positioned in the distal end of the needle with the suture extending through the slot. The stylus is held in a non-deployed position when the stylus is positioned inside of the needle. The blunt distal end of the stylus extends a distance toward the open distal end of the needle but it is retained within the shaft of the needle by a portion of the retainer held in one recess in the needle hub and by a position of the movable stop against the edge. When the movable stop is moved away from the edge, the blunt distal end of the stylus is deployed to move within the shaft of the needle. The stylus moves to contact the fastener and push the fastener out of the shaft. The distal end of the stylus extends through and beyond the sharp open distal end of the needle. The portion of the retainer is moved to and positioned in another recess in the needle hub, thereby rendering the safety needle assembly in a blunted condition. The stylus is configured to non-releasably couple to the needle to provide an unmovable position of the stylus with respect to the needle to maintain the blunted condition. The gastropexy kit also includes a suture retention hub coupled to a portion of each suture. The suture retention hub comprises a first base formed include an opening therein configured to hold the suture. The suture retention hub also comprises a second base coupled to the first base. The second base is formed to include an opening configured to hold the suture. The suture positioned in the opening of the first base and the opening of the second base is moveable relative to both the first base and the second base when the hub is positioned in an un-locked position. The suture positioned in the opening of the first base and the opening of the second base is non-moveable relative to both the first base and the second base when the hub is positioned in a locked position.

Additional features and advantages of the present invention will be revealed in the following detailed description. Both the foregoing summary and the following detailed description and examples are merely representative of the invention, and are intended to provide an overview for understanding the invention as claimed.

BRIEF DESCRIPTION OF THE DRAWINGS

FIG. 5 is a perspective view of another portion of a safety needle assembly of the gastropexy kit of the present invention, showing a stylus and its associated hub;

FIG. 6 is a side elevational view of the stylus and hub of FIG. 5, showing the flanges, each with a clip at a free end thereof;

FIG. 7 is a top plan view of the stylus and hub of FIG. 5, showing the flanges with clips;

FIG. 15 is a sectional view of FIG. 12, showing the clips of the flanges in the upper apertures of the needle hub; and FIG. 16 is a sectional view similar to FIG. 13, showing the clips of the flanges in the lower apertures of the needle hub, and the blunt distal end of the stylus positioned through the distal end of the needle to render the needle assembly in a blunted position.

FIG. 42 is a partial view of a patient's stomach wall, showing one desirable deployment of fasteners, and showing a desired area for forming a tissue opening or stoma;

FIG. 43A is a side elevational view of the needle assembly positioned through a patient's skin and into a patient's stomach, the fastener contained within the distal end of the needle in a non-deployed position and the suture positioned between the fastener and the suture retention hub on the patient's skin;

FIG. 43B is a side elevational view of the needle assembly positioned through a patient's skin and into a patient's stomach, the fastener deployed into the stomach from its previous position within the distal end of the needle, the suture positioned between the fastener and the suture retention hub on the patient's skin;

FIG. 44A is a side elevational view with a cross-sectional view of the suture retention hub positioned on a patient's skin and the handle of the hub positioned upward so that a suture is moveably positioned through the hub, an opposite end of the suture coupled to a fastener in the patient's stomach;

FIG. 44B is a side elevational view with a cross-sectional view of the suture retention hub positioned on a patient's skin and the handle of the hub positioned downward and generally parallel or planar to the upper surface of the hub, the suture tensioned and crimped within the hub, an opposite end of the suture coupled to a fastener in the patient's stomach, and the hub pulling the fastener closer to the patient's skin; and FIG. 44C is a side elevational view of the suture retention hub positioned on a patient's skin and the handle of the hub positioned downward and generally parallel or planar to the upper surface of the hub, the suture tensioned and crimped within the hub, an opposite end of the suture coupled to a fastener in the patient's stomach, and the hub pulling the fastener closer to the patient's skin.

DETAILED DESCRIPTION

Figure 1:
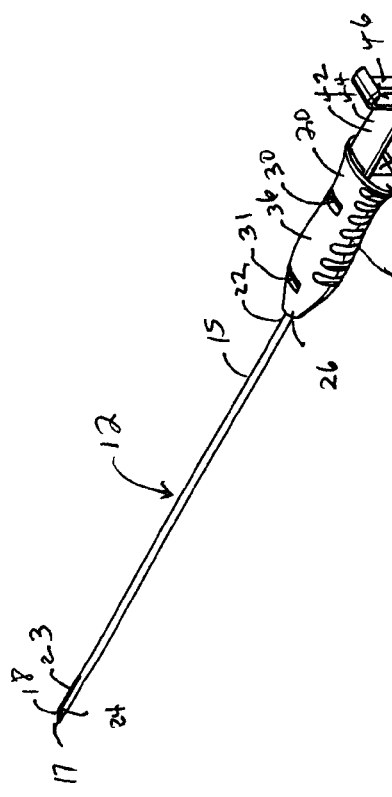
FIG. 1 is a perspective view of a portion of a safety needle assembly of the gastropexy kit of the present invention, showing the needle and its associated hub.
Figure 2:
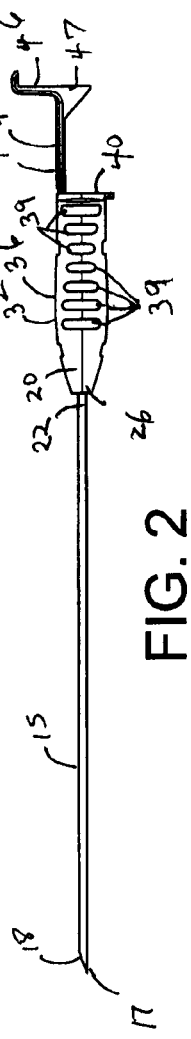
FIG. 2 is side elevational view of the portion of the safety needle assembly of FIG. 1, but showing one surface of the hub with apertures therein.
Figure 3:
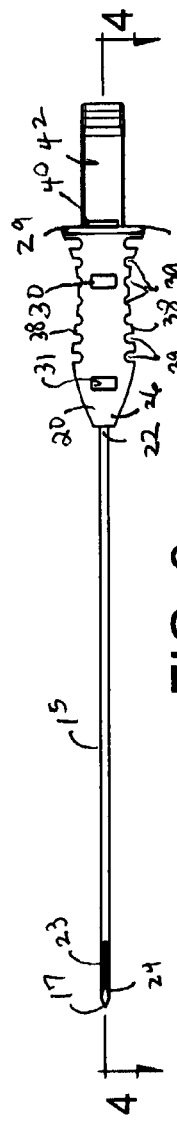
FIG. 3 is a top plan view of the portion of the safety needle assembly of FIG. 1, but showing another surface of the hub with grooves therein.

Reference will now be made in detail to one or more embodiments of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

For gastropexy, an apparatus is needed for holding and stabilizing in a position a portion of a patient's stomach, to permit a safe and accurate percutaneous tissue opening, namely, a stoma, into a patient's stomach. Such apparatus usually includes a needle which desirably carries a suture and fastener. An apparatus for applying tension to the suture is also desirably used as well. The present invention describes a desirable apparatus for performing gastopexy.

Turning now to a needle apparatus of a gastropexy kit, a safety needle assembly is provided. The safety needle assembly is rendered safe by positioning a blunt stylus therethrough, which results in blunting of the assembly.

Figure 4:
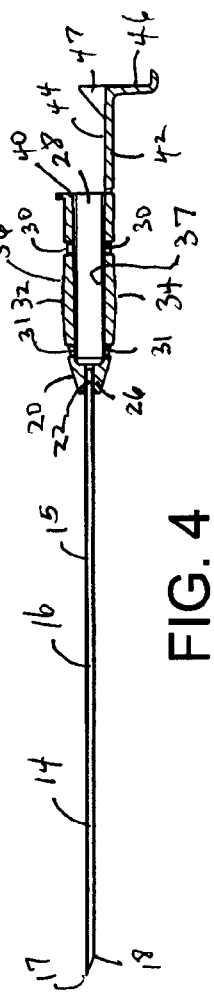
FIG. 4 is a sectional view of FIG. 3, taken at lines 4-4.

Referring now to FIGS. 1-16 in general, and 1-4 in particular, the present invention provides a safety needle assembly 10. The safety needle assembly 10 includes a metal needle 12 having an opening 14 extending through a metal shaft 15, which defines an inner surface 16 (FIG. 4). A tapered sharp tip 17 is positioned at a distal end 18 of the needle 12. A needle hub 20 is coupled at or near a proximal end 22 of the needle 12. A slot 23 may be formed desirably, but not by way of limitation, at a lower edge 24 of the tapered distal tip 16 of the needle 12.

A distal end 26 of the needle hub 20 is coupled about a portion of the proximal end 22 of the needle 12. The needle hub 20 includes an opening 28 that is continuous with the opening 14 that extends through the hollow shaft 15 of the needle 12 and through the distal tip 16 thereof. The needle hub 20 also desirably includes opposing spaced-apart edges 29 at a proximal end 40 thereof. The needle hub 20 desirably has a pair of upper apertures or upper recesses 30, one upper recess 30 positioned on each of the relatively flat sides 32, 34 on an outer surface 36 of the hub 20 near the proximal end 22 thereof. Another pair of lower apertures or lower recesses 31, one lower recess 31 positioned on each of the relatively flat sides 32, 34 on an outer surface 36 of the hub 20 and near the distal end 26 thereof. The apertures or recesses 30, 31 extend from the outer surface 36 to the opening 28 in the needle hub 20. The purpose for the apertures or recesses 30, 31 will be discussed in detail below.

An inner surface 37 (FIG. 4) is provided and is defined by opening 28 formed through the needle hub 20. The inner surface 37 is sized to receive a blunted stylus therethrough. The hub 20 includes a pair of relatively short sides 38 as well, which are spaced-apart from each other, but are adjacent to the flat sides 32, 36. Each short side 38 has a plurality of grooves 39 formed therein to facilitate gripping the hub 20.

The needle hub 20 also includes, at the proximal end 40, a handle 42 which desirably is positioned to extend away from the proximal end 40. The handle 42 desirably includes a handle shaft 44 generally axially aligned with the needle hub 20 and which is desirably integrally formed with the proximal end 40 of the needle hub 20. The handle 42 also desirably includes a handle portion 46 which extends at an angle, desirably at about a 90 degree angle, transversely away from the handle shaft 44. A pair of wedges 47 are positioned in a spaced-apart orientation on either side of a junction of the shaft 44 and the handle portion 46. The wedges 47 are positioned to function as stops, as will be described in further detail below. The needle hub 20 may also include a "C"-clip (not shown) to hold a suture which may be positioned at least partially in the needle 12.

The blunted safety needle assembly 10 also includes a stylus 50, as illustrated in FIGS. 5-7, having a solid or hollow shaft 52 sized to have an outer surface 54 which cooperates to substantially fill a diameter of the inner surface 28 of the needle 12. The stylus 50 includes a blunted, non-sharp, distal end 56 and a proximal end 58 which is coupled to a stylus hub 60. The distal end 56 is sized and configured to position against and move a fastener positioned near the distal tip in the shaft 15 of the needle 12.

The stylus hub 60 includes, at one end, a cylindrical upper hub 62 which desirably includes a standard luer lock. At an opposite end of the upper hub 62 is a narrower-diameter lower hub 64 which desirably couples about at least a portion of the proximal end 58 of the stylus 50. A protruding rim or ridge 63 which extends about a circumference of the junction of the upper hub 62 and the lower hub 64. A pair of flanges 68 extend from the lower hub 64 and include free ends 72 which extend away from the upper hub 62 and toward the distal end 56 of the stylus 50, but are in a substantial axial alignment therewith. The flanges 68 flare slightly away from the stylus shaft 52. Generally triangularly-shaped (in side view) clips 74 (FIG. 6) extend outward on an outer surface 76 of each flange 68 at each free end 72 of the flange 68. The flanges 68 and clips 74 thereon provide a retainer. It will be understood that at least a portion of the stylus hub 60, that is, at least the flanges 68, is sized to extend into and contact the inner surface 37 of the needle hub 20 (FIGS. 15 and 16). The stylus 50 may include an opening 78 through hubs 60, 64 and the shaft 52 of the stylus 50.

Figure 8:
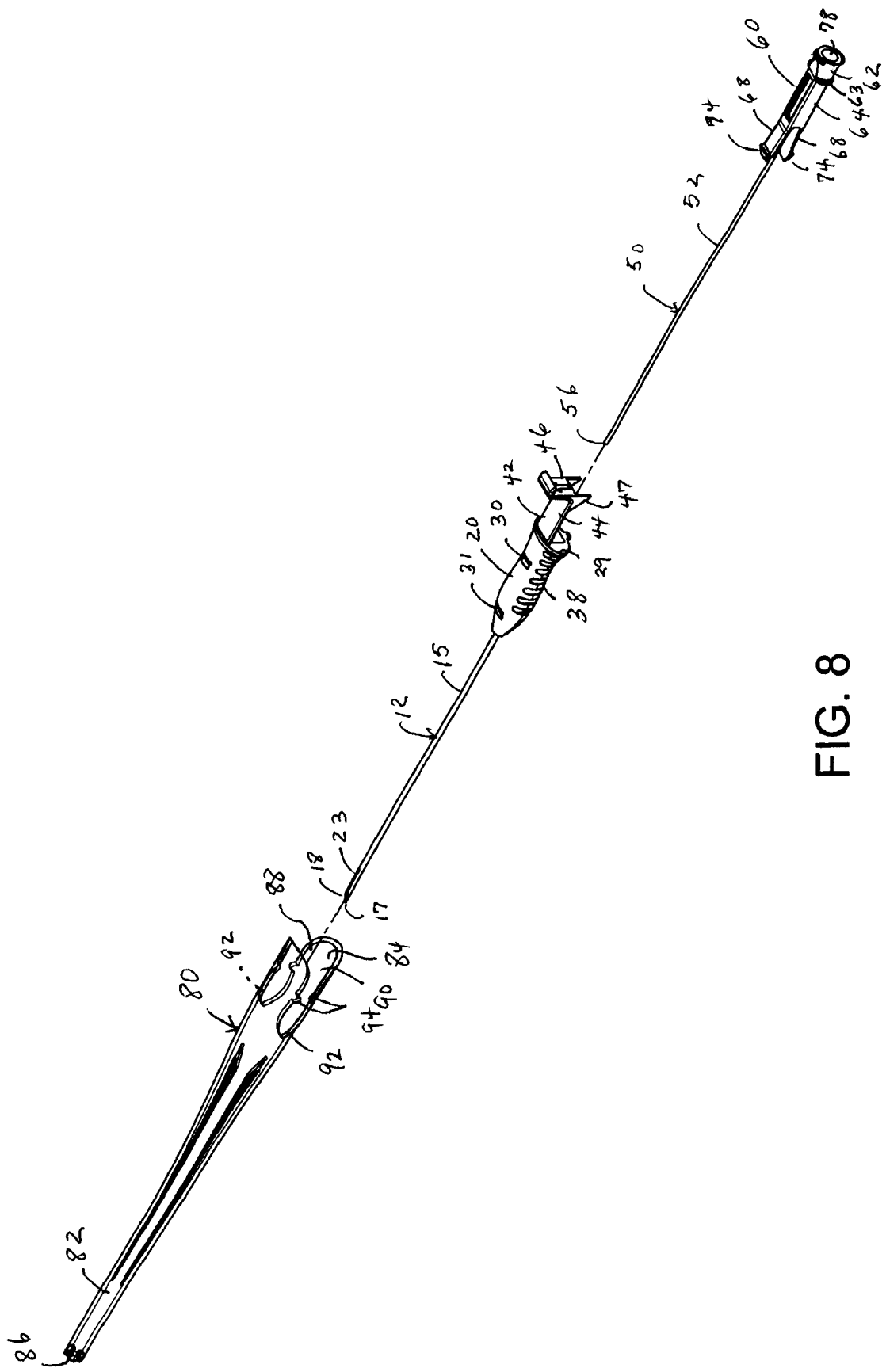
FIG. 8 is an exploded perspective view of a portion of the gastropexy kit, including the safety needle assembly and including a sheath.
Figure 9:
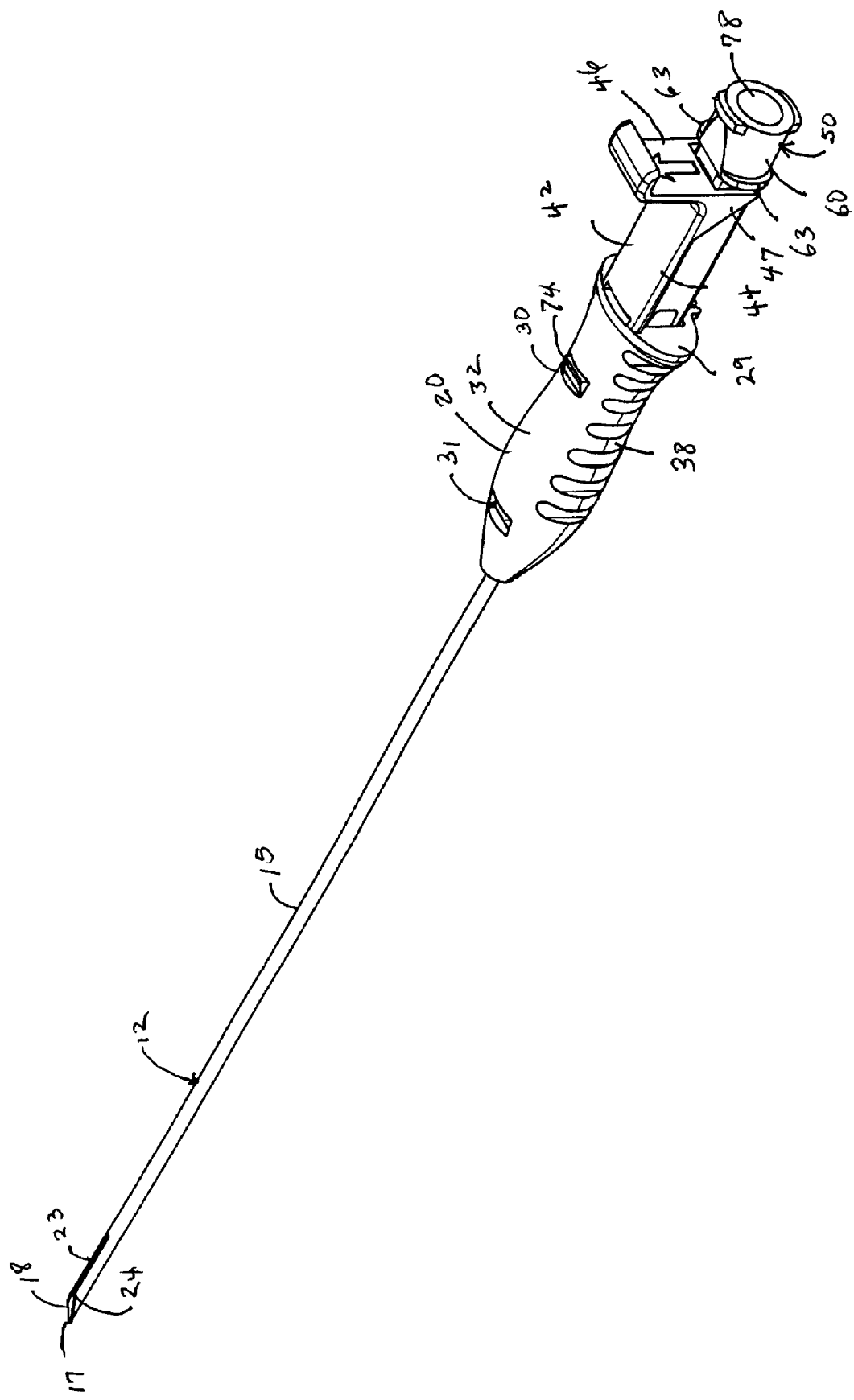
FIG. 9 is a perspective view of the safety needle assembly of the gastropexy kit, showing the stylus positioned in at least a portion of the needle.
Figure 10:
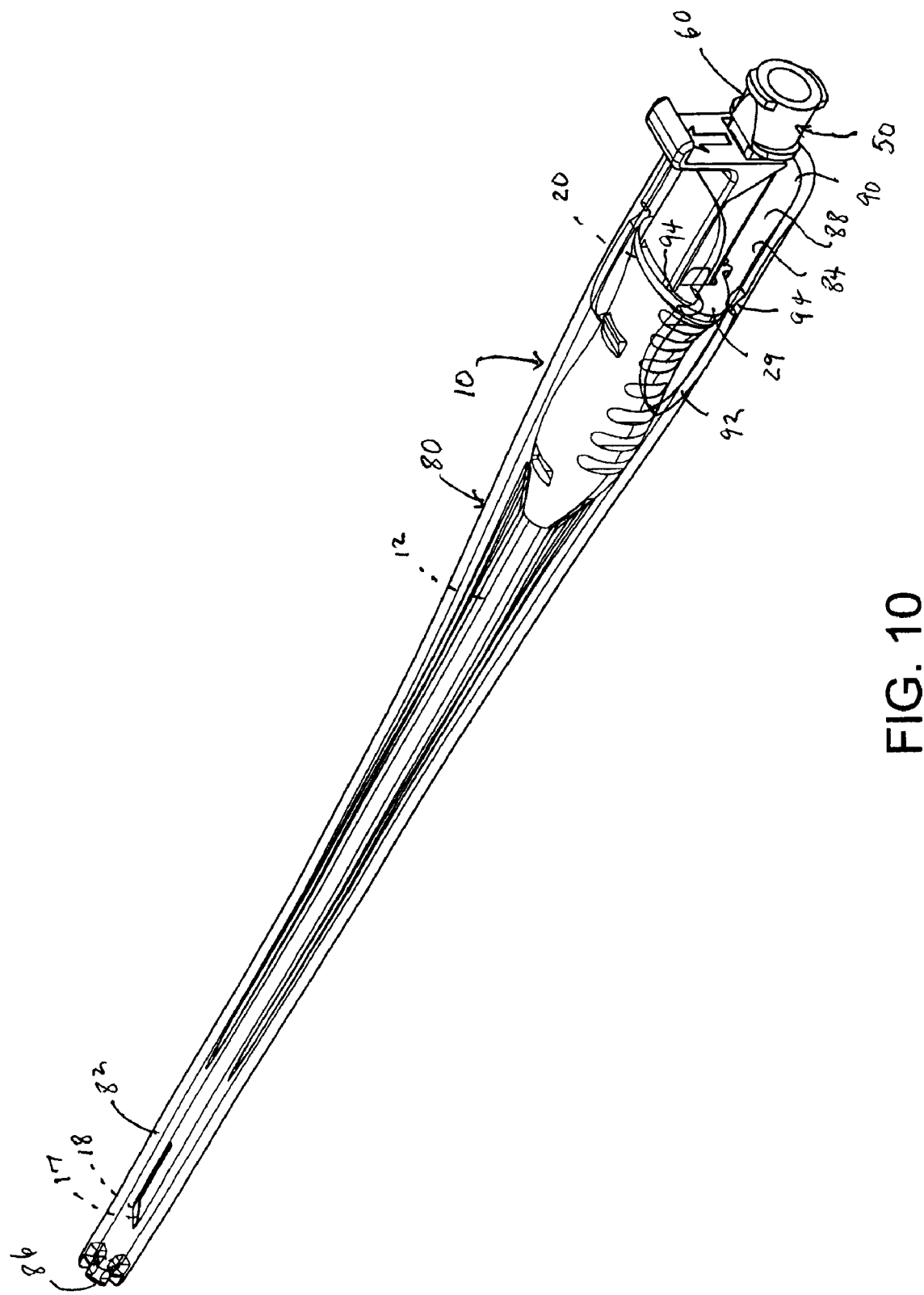
FIG. 10 is a perspective view of the safety needle assembly of the gastropexy kit positioned in the sheath.
Figure 11:
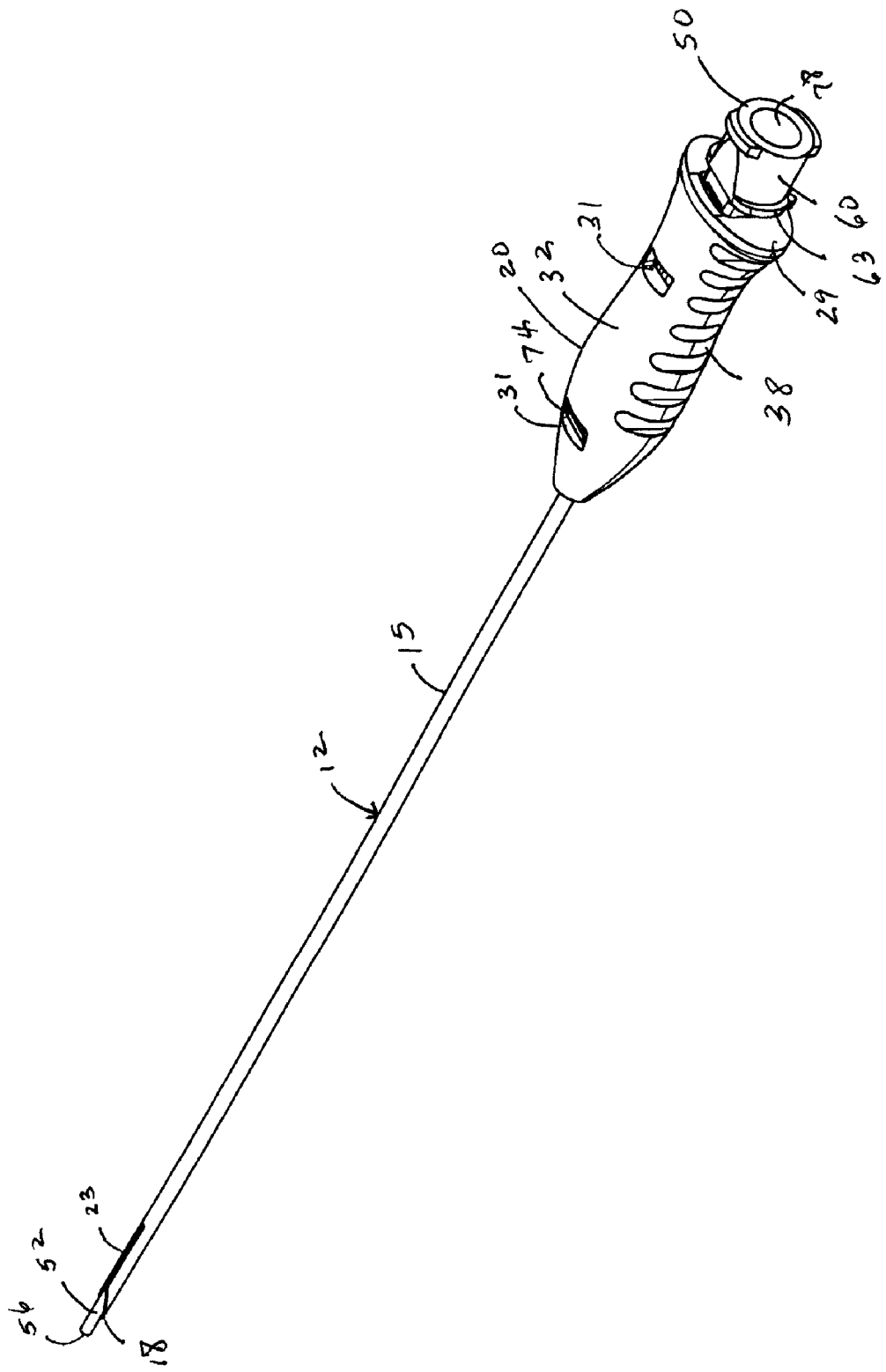
FIG. 11 is a perspective view of the safety needle assembly of the gastropexy kit, showing the stylus extending through the needle, thereby rendering the needle blunt.
Figure 12:
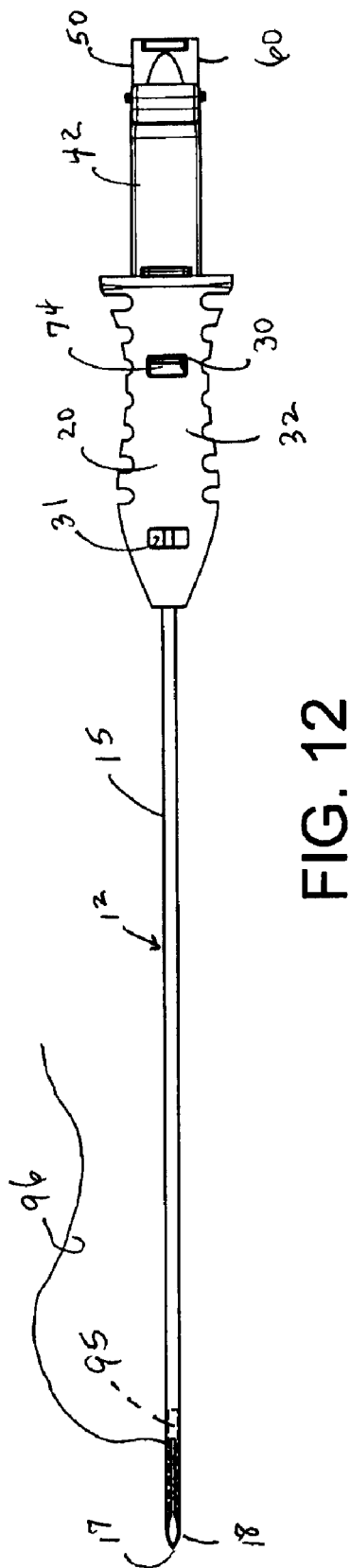
FIG. 12 is a top plan view of the safety needle assembly of the gastropexy kit, showing the stylus in the needle a T-bar fastener positioned therein (shown in phantom lines), a suture extending from the T-bar fastener and through the slit in the needle.
Figure 13:
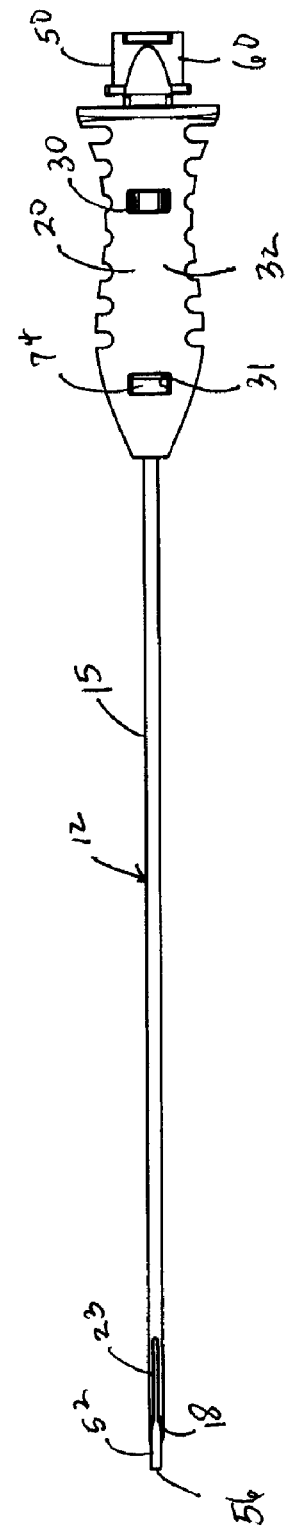
FIG. 13 is a top plan view of the safety needle assembly of the gastropexy kit, but showing the stylus extending through the needle to render the assembly in a blunted position.
Figure 14:
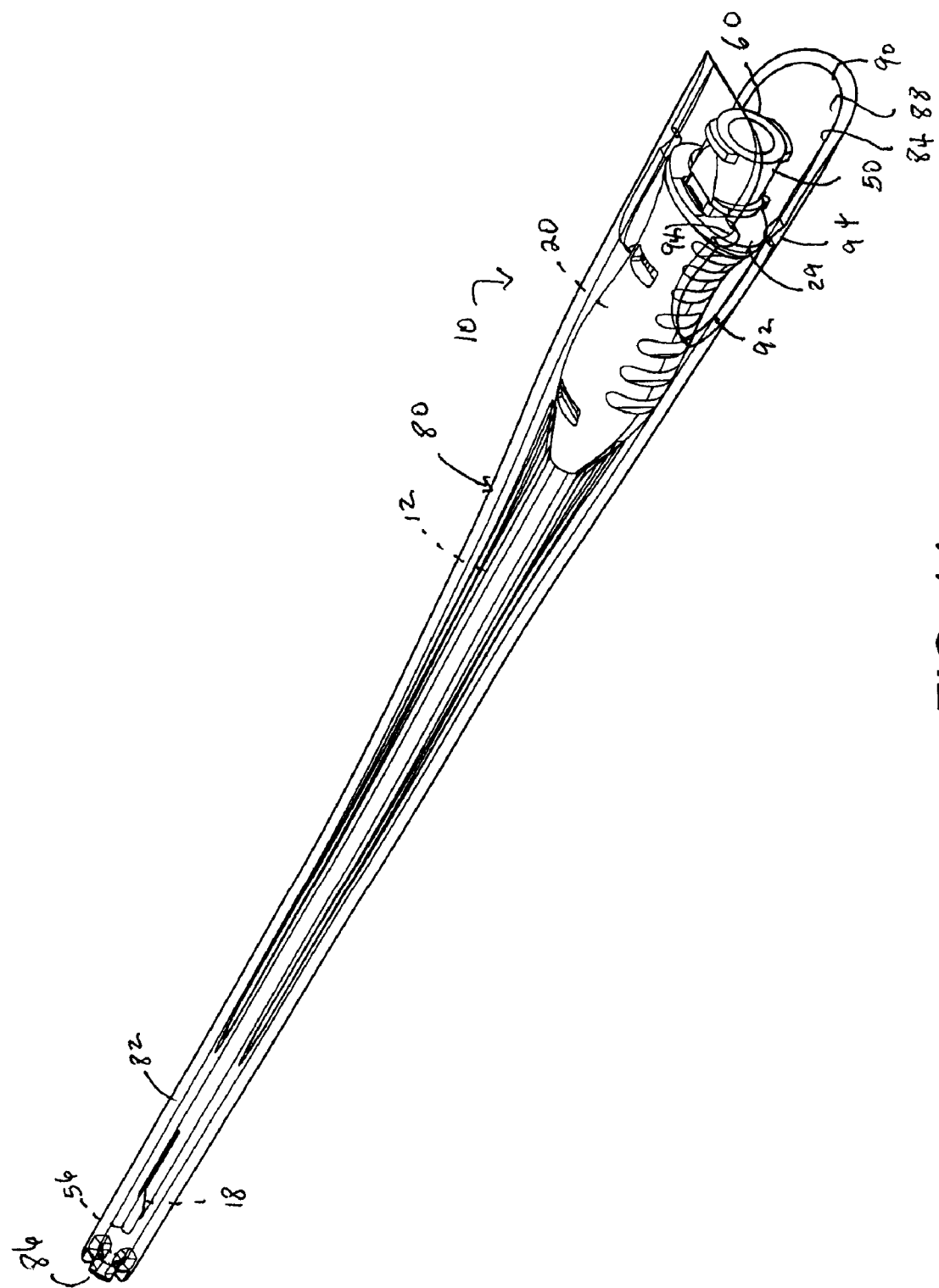
FIG. 14 is a perspective view of the safety needle assembly of the gastropexy kit of FIG. 13, but shown positioned in the sheath.
Figure 17:
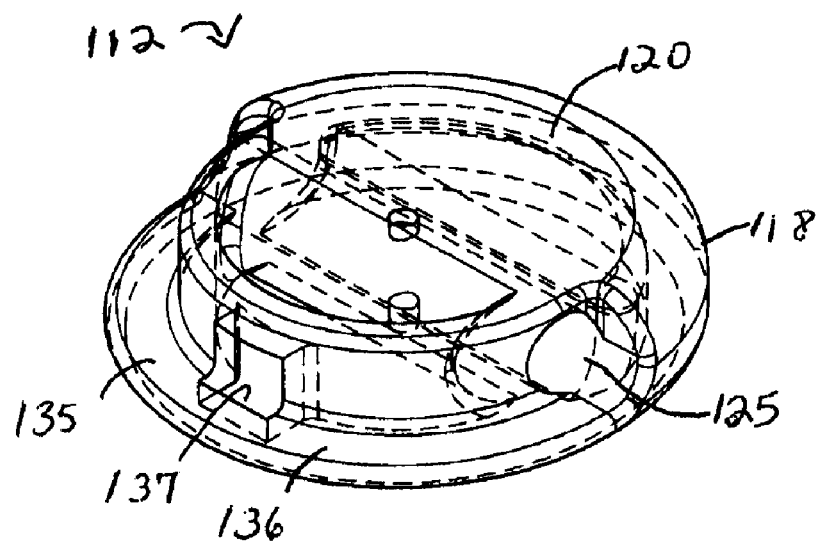
FIG. 17 is a perspective view of a top of a base or first base of a suture retention hub of the gastropexy kit of the present invention.
Figure 18:
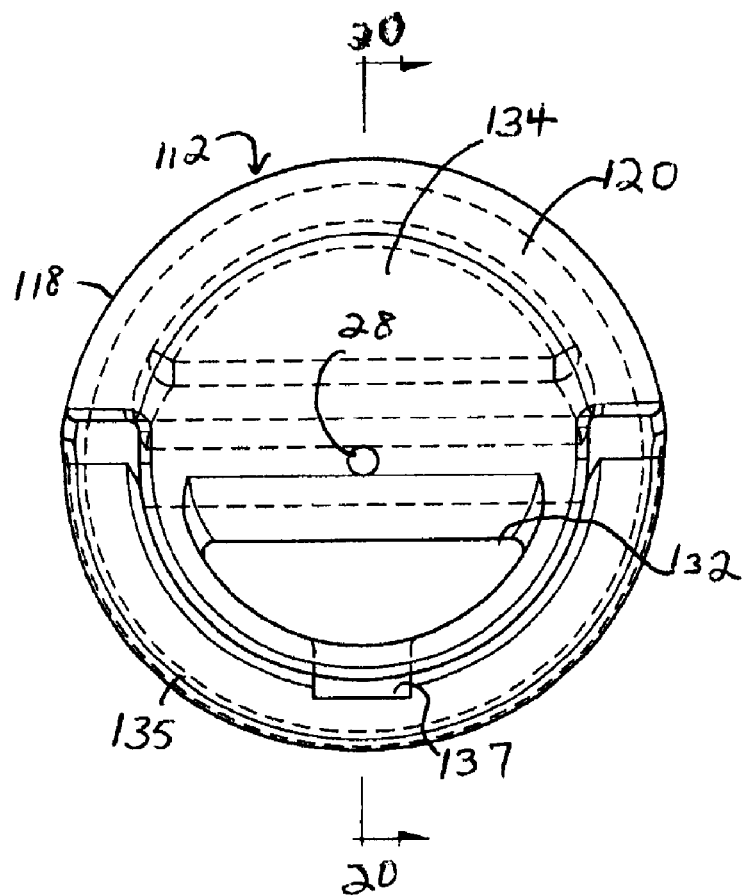
FIG. 18 is a top plan view of the base or first base of FIG. 17.
Figure 19:
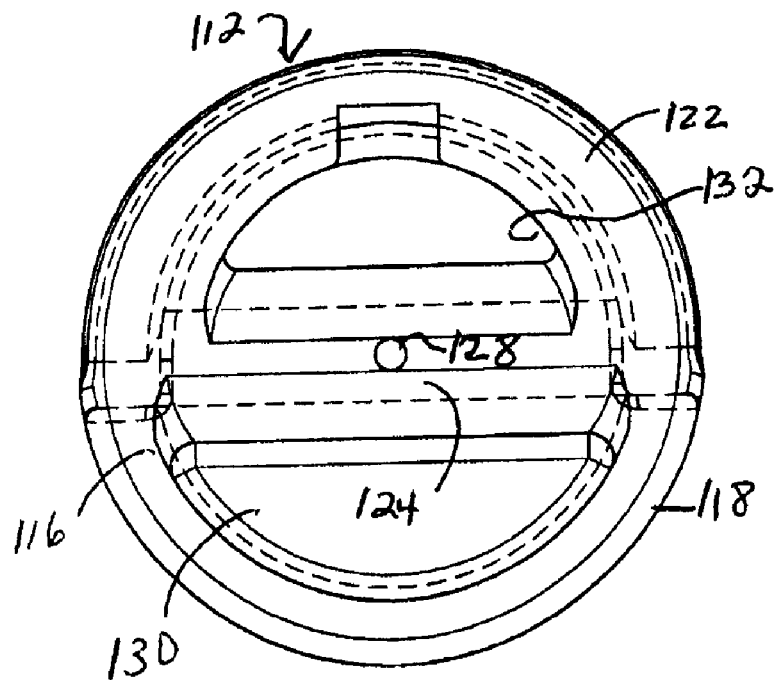
FIG. 19 is a bottom plan view of the base or first base of FIG. 1.
Figure 20:
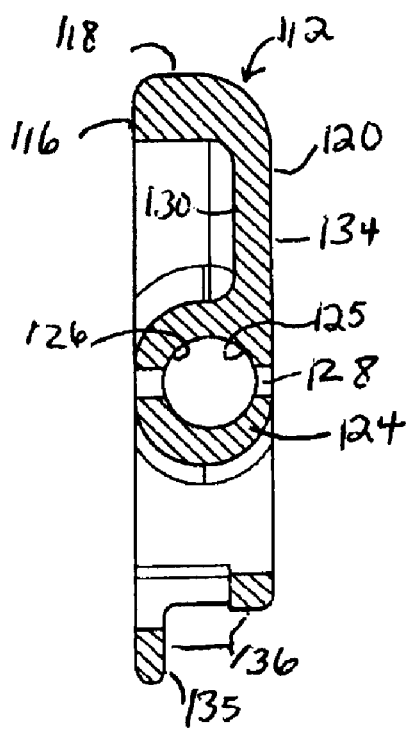
FIG. 20 is a sectional view of FIG. 18 taken along lines 20-20.
Figure 21:
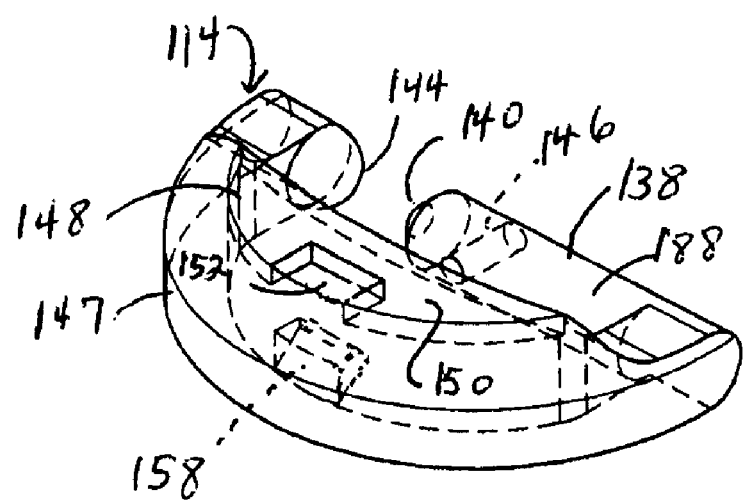
FIG. 21 is a perspective view of a top of a handle or second base of a suture retention hub of the gastropexy kit of the present invention.
Figure 22:
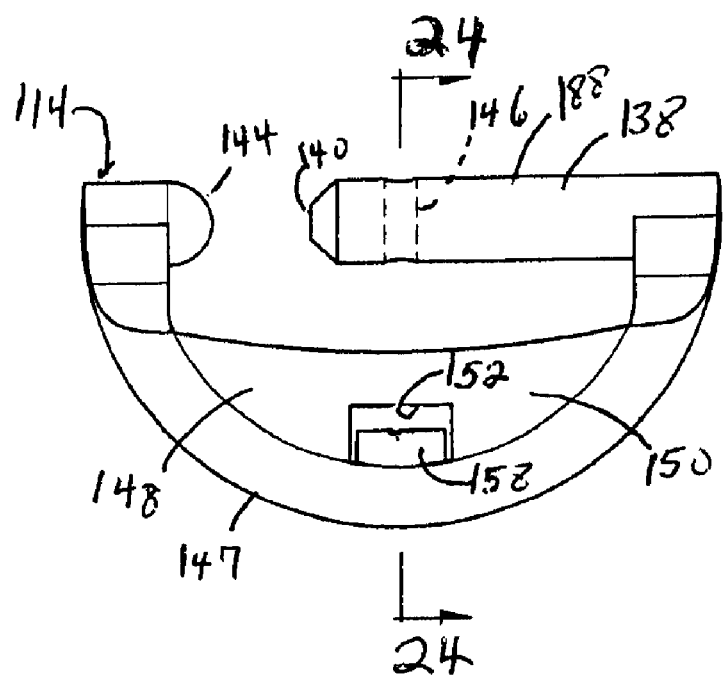
FIG. 22 is a top plan view of the handle or second base of FIG. 21.
Figure 23:
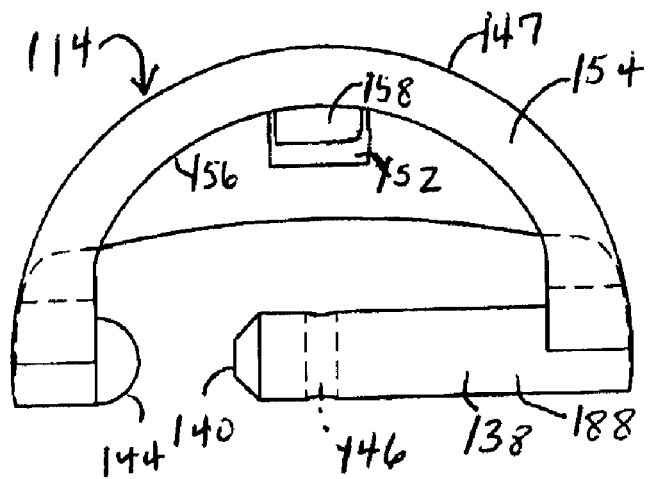
FIG. 23 is a bottom plan view of the handle or second base of FIG. 21.
Figure 24:
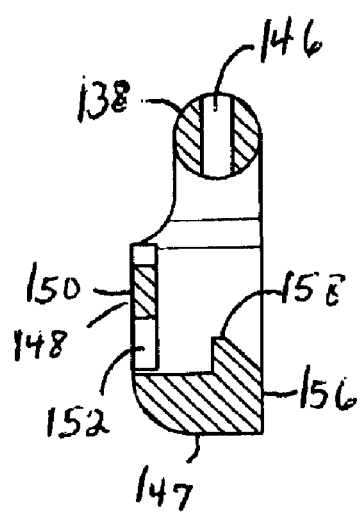
FIG. 24 is a sectional view of FIG. 22 taken along lines 24-24.
Figure 25:
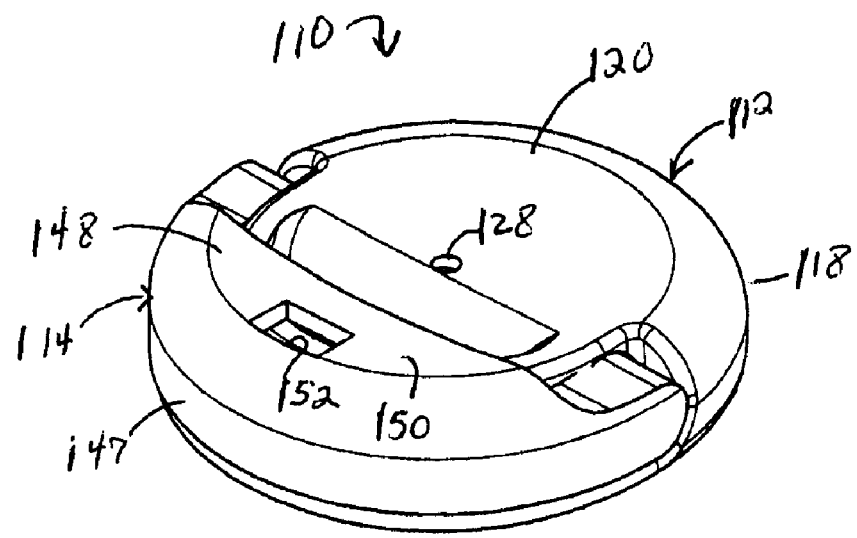
FIG. 25 is a perspective view of a top of the suture retention hub of the gastropexy kit of the present invention, showing both the base or first base and the handle or second base.
Figure 26:
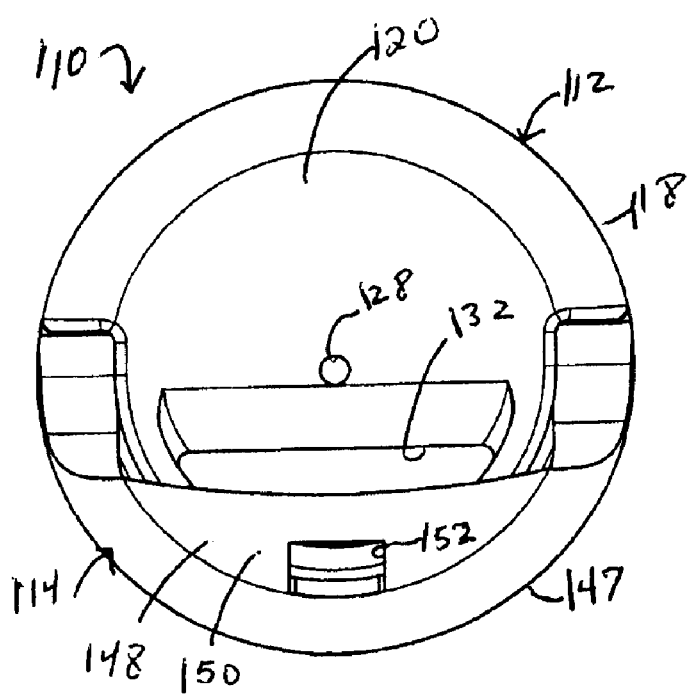
FIG. 26 is a top plan view of the suture retention hub of FIG. 25.
Figure 27:
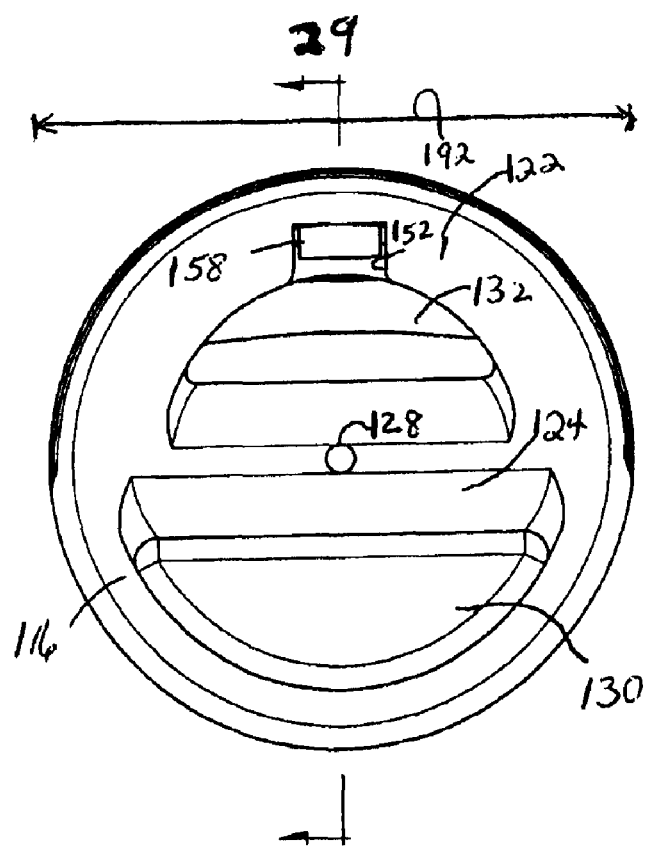
FIG. 27 is a bottom plan view of the suture retention hub of FIG. 25.
Figure 28:
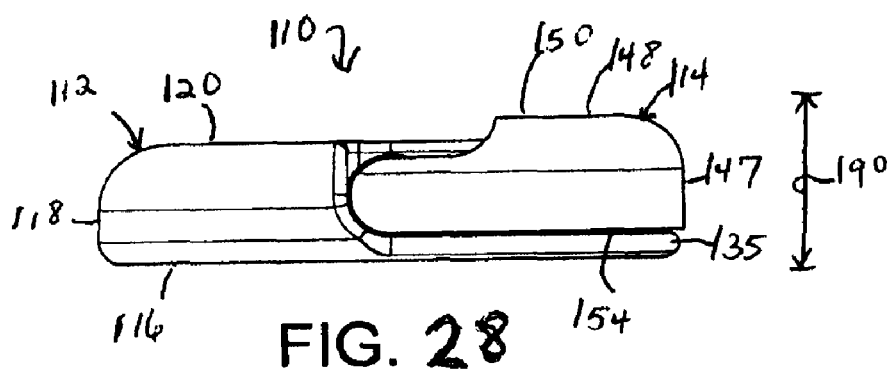
FIG. 28 is an elevated side view of the suture retention hub of FIG. 25.

A protective sheath 80, as shown in FIGS. 8, 10 and 14, may be provided, to isolate the sharp tip 17 of the end 18 of the needle 12 and protect the health care provider, until such time as the safety needle assembly 10 is removed from the sheath 80 for use. The sheath 80 is sized to hold the needle 12 with the stylus 50 positioned therewith. The sheath 80 has an outer surface 82 and an inner surface 84, and is shaped generally like a funnel having one enclosed end. The blunted safety needle assembly 10 is desirably positioned in the sheath 80, with the sharp tip 17 of the distal end 18 of the needle 12 positioned in a closed end 86 of the sheath 80, and the needle hub 20 and stylus hub 50 accessible through an opening 88 in an open end 90 of the sheath 80. Slots 92 are positioned adjacent the opening 88 in an opposing, spaced-apart position. Each slot 92 is flanked by a pair of protuberances 94 formed along an edge 96 forming each slot. When a needle assembly 10 is positioned in the sheath 80, the edge 29 of the needle hub 20 are desirably positioned in the slots 92 and beneath the protuberances 94. The protuberances 94 catch the rims 29 of the hub 20, thereby preventing the needle assembly 10 from falling out of the sheath 80. In this manner, the needle assembly 10 is releasably held in the sheath 80 until a health care provider removes the needle assembly 10 from the sheath 80. Once the needle assembly 10 has been used, it may be stored in the sheath 80 (FIG. 14). It will be appreciated that the sheath 80 is formed from a material having resilient qualities, which permits the sheath to operate as shown and/or described herein.

Turning now to an apparatus for applying tension to the suture, a suture retention hub is provided, for use in performing gastropexy. The suture retention hub desirably is used to hold a tensioning filament or suture on an external portion of a patient's skin, and may be used to provide tension to an internally disposed device via a suture. Such a device may include, for example, but not by way of limitation, a "T-bar" fastener or other fastener (not shown) which is positioned internally in a patient's stomach in a gastropexy procedure. Referring now to FIGS. 17-38 in general, and 17-32 in particular, a suture retention hub 10 is illustrated. The hub 110 includes a first base or base 112 and a movable, pivotal second base or handle 114. The first base or base 112, as shown in FIG. 17-20, includes a lower surface 116 (FIG. 19) having a substantially circular outer perimeter 18, and an upper surface 120.

A portion 122 (FIG. 19) of the perimeter 118 of the base 112 adjacent the lower surface 116 is constructed to have a flat wheel or disk-like appearance. A bar 124 is provided and extends across the lower surface 116 from perimeter 118 to perimeter 118 of the base 112. The bar 124 has an opening 125 which extends therethrough which defines an inner surface 126. The bar 124 also has an aperture 128 formed transversely therethrough. On one side of the bar 124, an indentation 130 is provided between the bar 124 and the perimeter 118 of the base 112 on the lower surface 116. On the opposite side of the bar 124, an opening 132 extends between the bar 124 and the perimeter 118. The opening 132 extends from the lower surface 116 through the upper surface 120 of the base 112.

An outer portion of the upper surface 120 of the base 112 generally has a circular perimeter and the upper surface 120 includes a semi-circular raised flat surface 134. The opening 128 through the base 112 is generally, for example, desirably generally semi-circular in configuration, being defined between a portion of the perimeter 118 and the bar 124. An edge 135 of the perimeter 118 is adjacent the opening 128, and provides an L-shaped flange 136 along a portion of the perimeter 118 on the upper surface 120. The L-shaped flange 136 includes an opening 137 therein.

The pivotal second base or handle 114, as illustrated in FIGS. 21-24, couples to the base 112 via a pivot pin 138. The pivotal second base or handle 114 is also of a generally semi-circular configuration, and includes a pivot pin 138 having a boss 140 at a free end thereof. The pivot pin 138 and boss 144 are in an axial alignment with an opposing, spaced-apart boss 144 formed on a portion of the second base or handle 114. The pivot pin 138 has an aperture 146 formed therethrough. The aperture 146 may be generally in an axial alignment with the aperture 128 positioned transversely through the bar 124 of the base 112 when the second base or handle 114 is pivoted into a transverse position relative to the upper surface 120 of the base 112.

Figure 29:
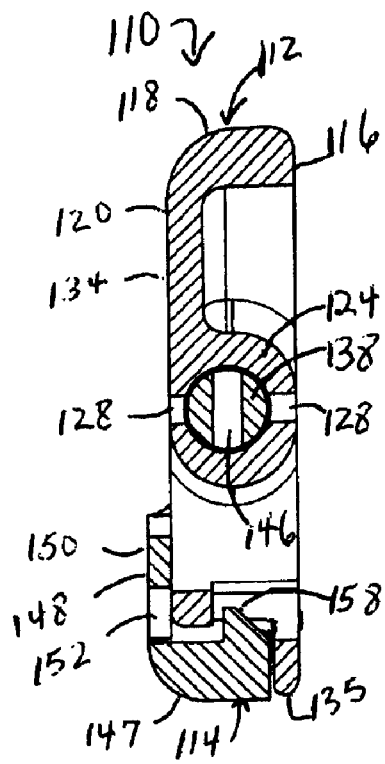
FIG. 29 is a sectional view of FIG. 27 taken along lines 29-29.
Figure 30:
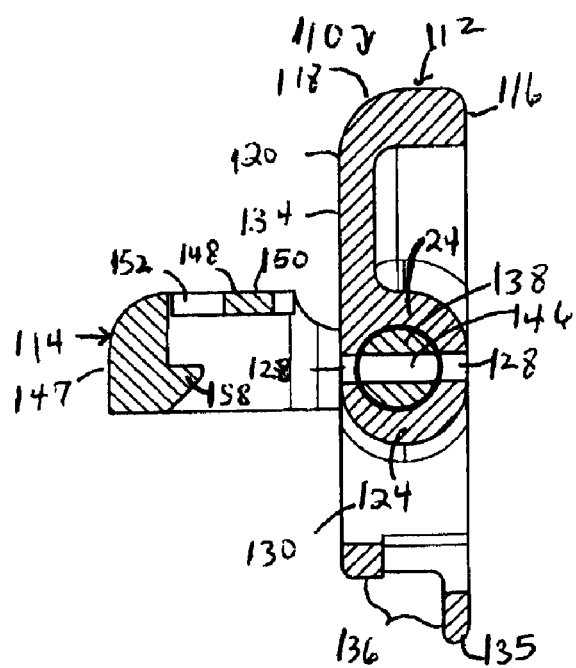
FIG. 30 is a sectional view similar to FIG. 29, but showing the position of the apertures with the handle or second base positioned transversely relative to the base or first base, showing the alignment of the apertures in the handle or second base and the base or first base.

The second base or handle 114 includes a perimeter 147 and an upper surface 148 which desirably includes a lip 150 formed to include a small opening 152 therein. On a lower surface 154 of the second base or handle 114, an inner edge 156 of the perimeter 147 includes a knob 158 positioned thereon. The second base or handle 114 is formed from a material which has some resiliency. Therefore, at least portions of the second base or handle 114 may resiliently bend to permit assembly with the base 112. When assembled, the pivot pin 138 of the second base or handle 114 is positioned in the opening 125 of the bar 124 of the base 112 (FIG. 29). The second base or handle 114 is moveable or pivotable with respect to the base 112 when in an opened position (FIG. 30). The second base or handle 114 is frictionally held in a non-pivoting position when the second base or handle 114 is positioned against the flange 136 and the knob 158 is positioned through the opening 137 of the flange 136. The knob 158 and the opening 137 cooperate to provide a latch assembly for locking and un-locking the hub 110, thereby positioning and holding the second base or handle 114 in a locked position (FIG. 29) relative to the base 112. In this position, the aperture 146 formed through the pivot pin 138 is moved out of its general axial alignment (which occurs when the second base or handle 114 is positioned transversely at a about a 90 degree angle relative to the upper surface 120 of the first base or base 112). That is, the aperture 146 positioned through the pivot pin 138, in the locked position, is positioned at about a 90 degree angle with respect to the aperture 128 in the bar 124 of the first base or base 112.

The hub 110 may include a soft outer cover 160, as illustrated in FIGS. 33-38. The cover 160 is desirably, but not by way of limitation, a one piece cover 160 that is soft and has some resiliency to allow it to stretch to fit over the hub 110. Such a soft outer cover may be constructed from, for example, but not by way of limitation, a medical grade thermoplastic polyurethane. This type of material is desirably used to disburse the pressure from tension on the hub 110 against a patient's skin, thereby reducing the possibility of the hub 110 causing the development of a pressure sore or necrosis occurring under the hub 110.

The cover 160 desirably is generally disk-shaped, with a lower outer surface 162, an outer perimeter 164 and an upper outer surface 166. The cover 160 may desirably include an opening 168 and a flap 170 formed adjacent the opening 168. The hub 110 is desirably positioned through the opening 168 and the lower surface 116 of the base 112 of the hub 110 is positioned against an inner surface 172 and adjacent the lower surface 162 of the cover 160. The hub 110 may be substantially encompassed by the cover 160. The hub 110 is positioned such that the second base or handle 114 is desirably positioned adjacent the opening 168 in the upper surface 166 of the cover 160. The cover 160 includes an aperture 174 positioned through the lower surface 162 and a slit 176 positioned through the flap 170 of the upper surface 166 of the cover 160. The aperture 174 and the end of the slit 176 of the cover 160 are desirably generally aligned with the aperture 128 positioned through the bar 124 of the base 112.

Figure 31:
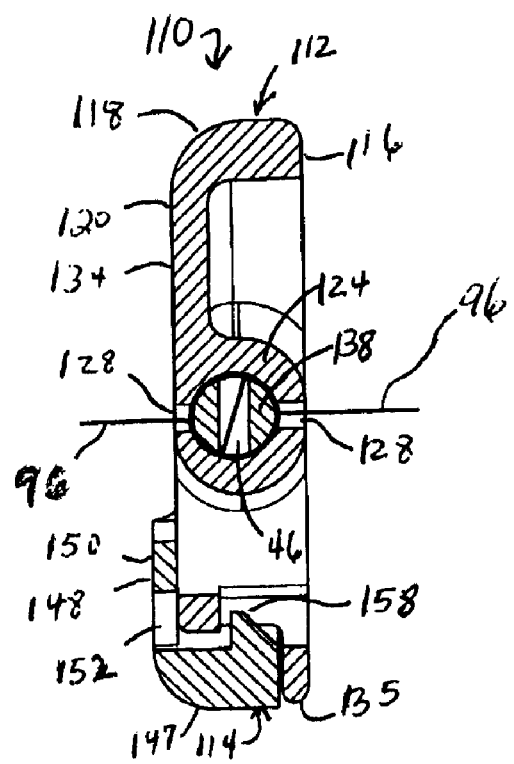
FIG. 31 is a sectional view similar to FIG. 29, but showing a suture positioned through the apertures in the base or first base and the handle or second base, showing the circuitous, crimped position of the aperture.
Figure 32:
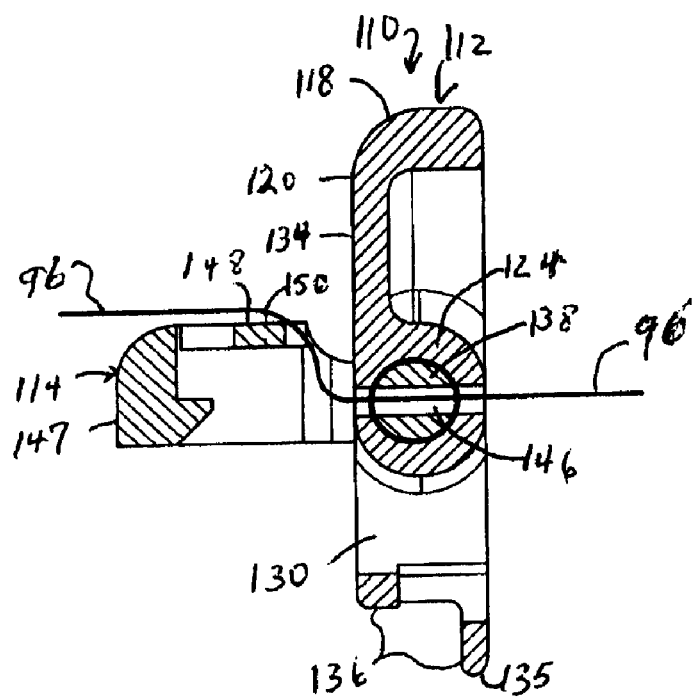
FIG. 32 is a sectional view similar to FIG. 30, but showing a suture positioned through the apertures in the base or first base and the handle or second base, showing the substantial axial alignment of the suture in the apertures.
Figure 33:
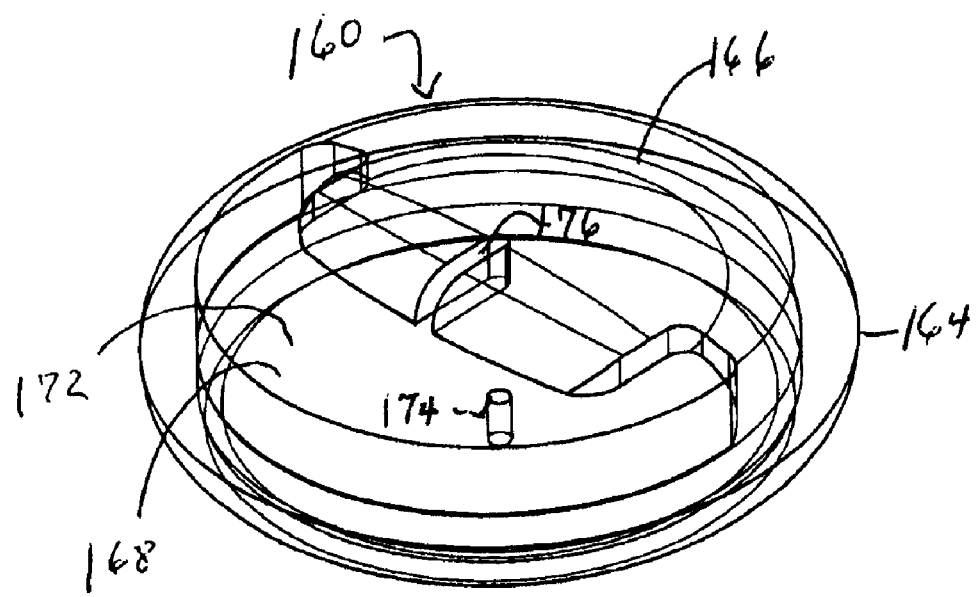
FIG. 33 is a perspective view of a top of a cover for the suture retention hub.
Figure 34:
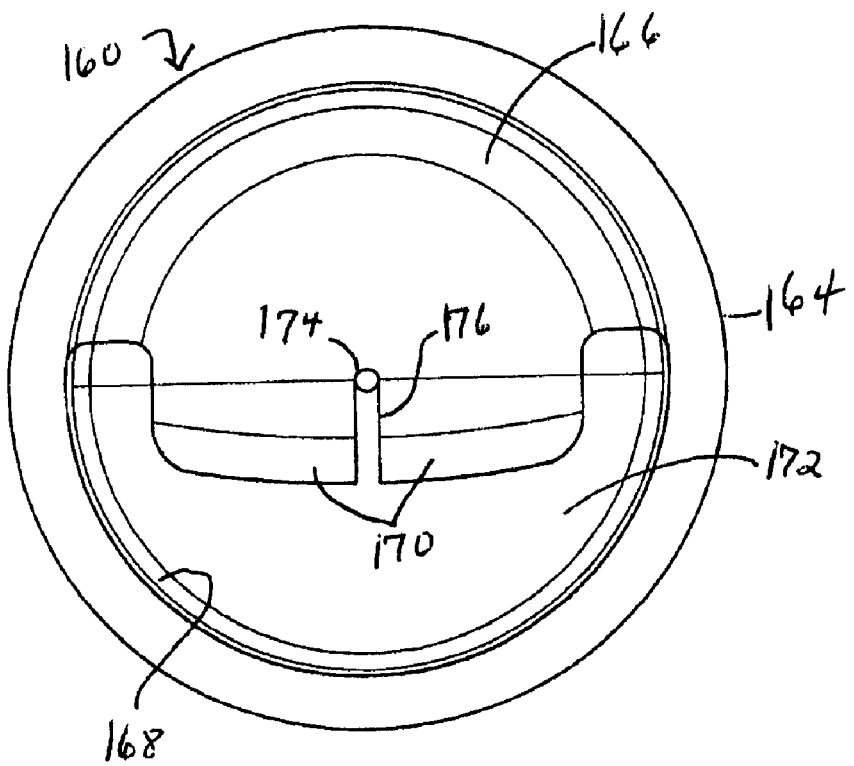
FIG. 34 is a top plan view of the cover of FIG. 33.
Figure 35:
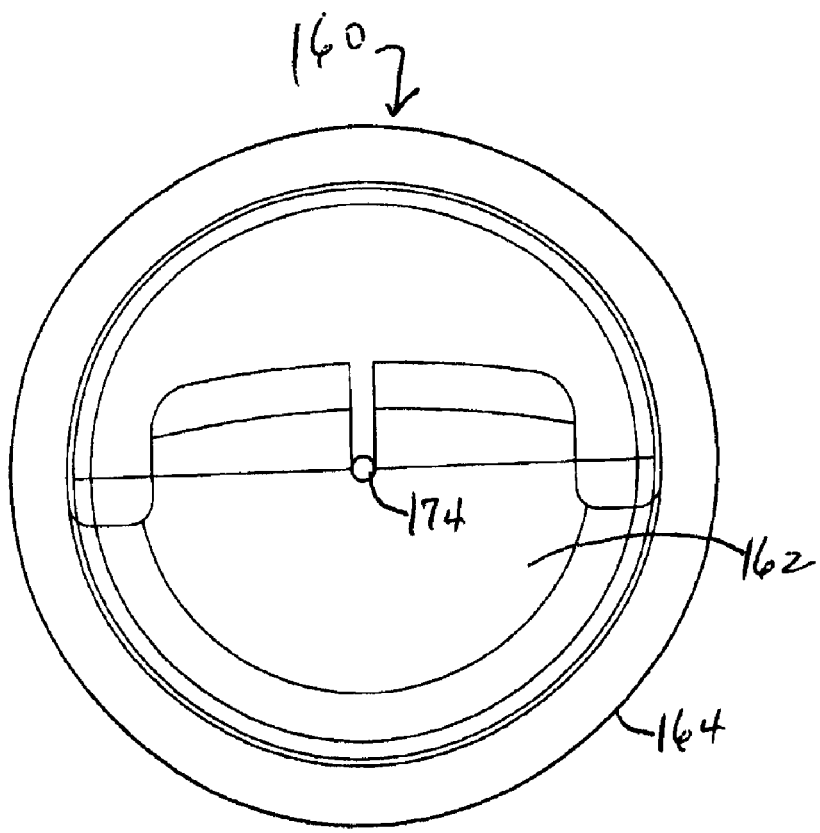
FIG. 35 is a bottom plan view of the cover of FIG. 33.
Figure 36:
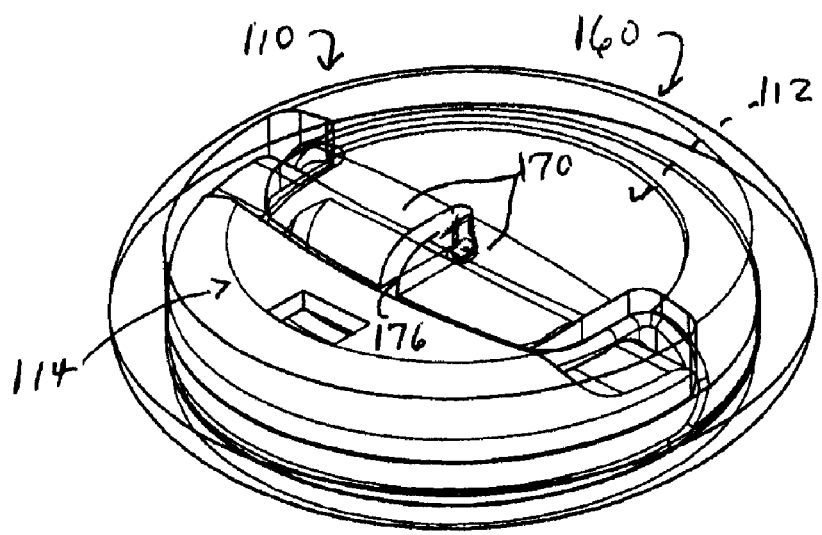
FIG. 36 is a perspective view of the cover of FIG. 33, but with a suture retention hub positioned therein.
Figure 37:
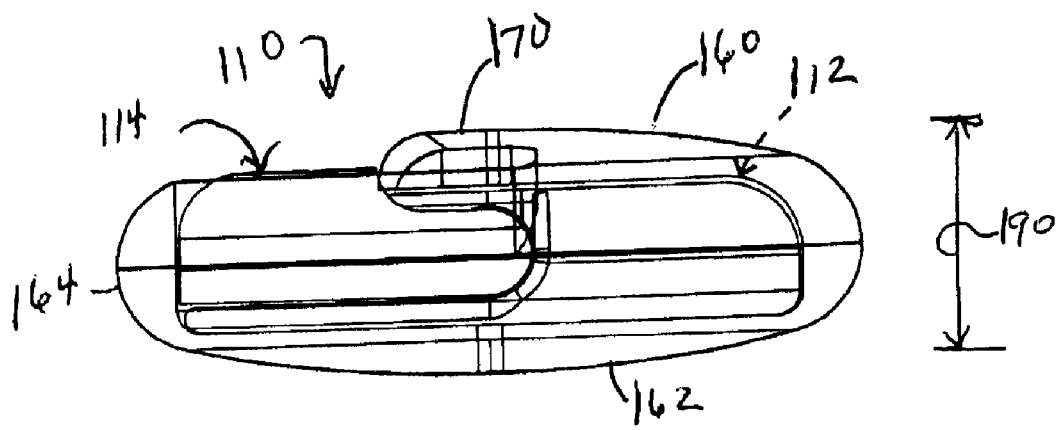
FIG. 37 is side view of the cover of FIG. 33 with the suture retention hub positioned therein.
Figure 38:
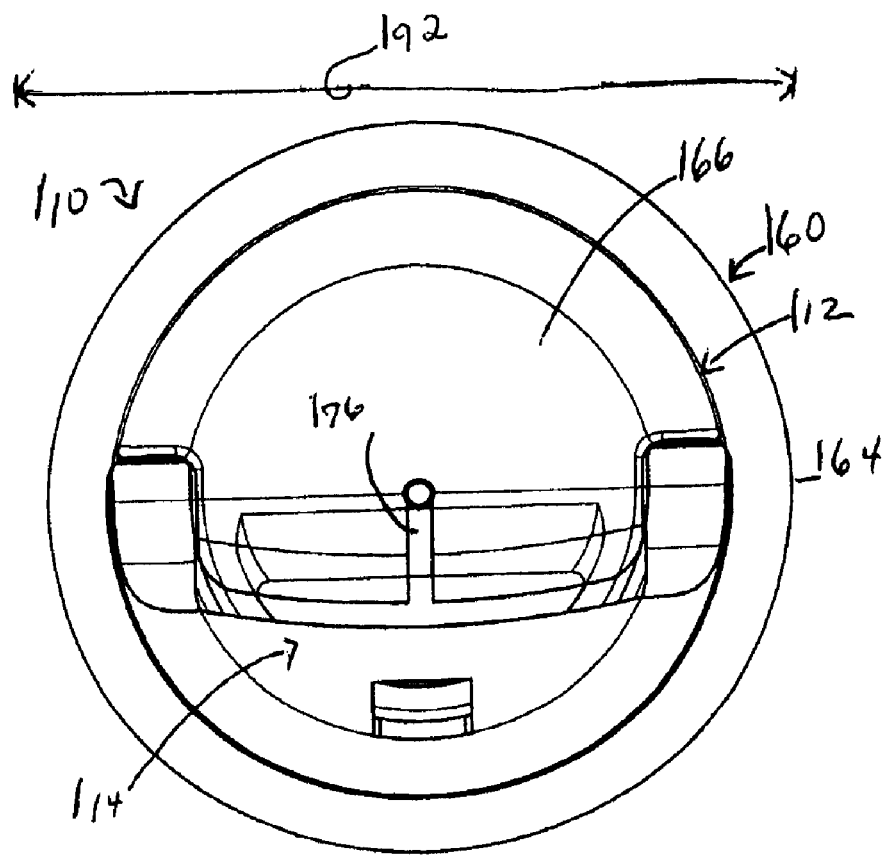
FIG. 38 is a top plan view of the cover of FIG. 33 with the suture retention hub positioned therein.
Figure 39:
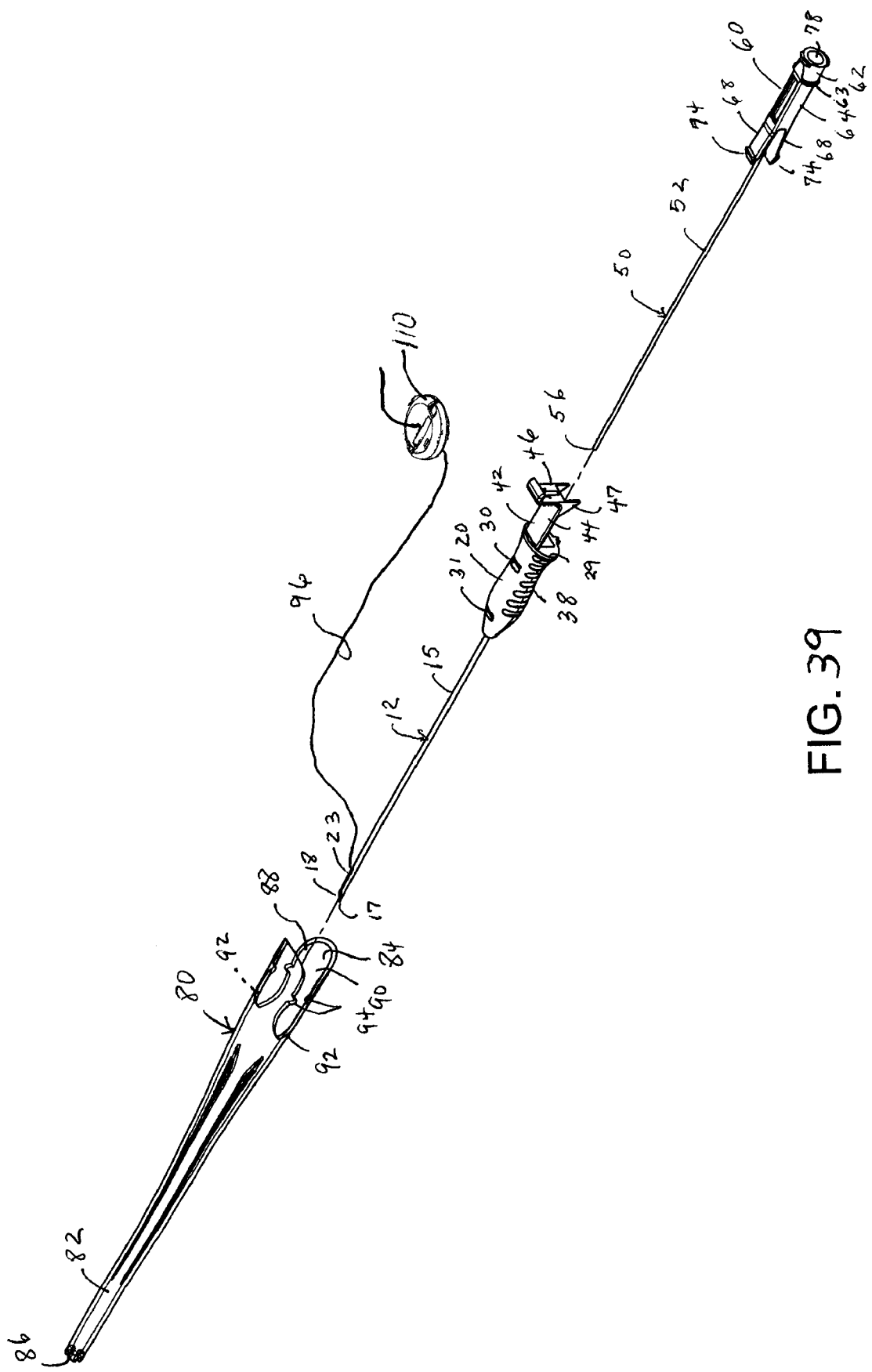
FIG. 39 is an exploded perspective view of components of the gastropexy kit.

Desirably a suture 96 is positioned through the aperture 128 in the bar 124 of the base 112, and through the aperture 146 of the pivot pin 138 of the second base or handle 114, as shown in FIGS. 31 and 32. The suture 96 is also positioned through the aperture 174 and the slit 176 in the cover 160 (not shown).

When it is desired to pull a portion of the suture 96 through the hub 110, as illustrated in FIG. 32, the suture 96 moves relatively easily through the hub 110 when the hub 110 is in an un-locked position. That is, the suture 96 passes through the aperture 128 in the bar 124 and the aperture 146 in the pivot pin 138, when the second base or handle 114 is positioned at an angle, desirably at substantially a 90 degree angle, relative to the upper surface of the base 112. In this position, the aperture 146 in the pivot pin 138 of the second base or handle 114 and the aperture 128 in the bar 124 of the base 112 are in a substantially axial alignment. Further, the aperture 174 and slit 176 in the cover 160 are also in a substantially axial alignment.

When it is desired to hold the suture 96 in its position in the hub 110, the hub 110 may prevent movement of the suture 96 and frictionally crimp the suture in an unmovable position when the hub 110 is positioned in a locked position, as shown in FIG. 31. That is, the when the second base of handle 114 is positioned substantially parallel or planar to the upper surface 120 of the base or first base 112, the suture 96 is prevented from moving. This is due to the aperture 146 in the pivot pin 138. Therefore, the suture 96 therein is positioned at an angle, and desirably substantially a 90 degree angle, relative to the aperture 128 in the bar 124 in the first base or base 112 and the suture 96 positioned therein, and may crimp the suture 96 against the inner surface 126 of the bar 124 as well.

For example, when the suture 96 is to be tensioned, the suture 96 is not movable relative to the hub 110 when the second base or handle 114 is positioned in the closed, locked position. The suture 96 greatly resists pressure to move through the hub 110 when positioned in this frictional, crimped, non-aligned position, which essentially locks the suture 96 in a non-moveable position against a device, such as a fastener 95, which may be positioned on the opposite end of the suture 96. That is, the hub 110 will hold the suture 96 in a position until an excess of 3 pounds of pressure is applied to the suture 96.

In a method of use of the gastropexy kit, a plurality of safety needles assemblies, each having a fastener loaded therein, each fastener coupled to a resorbable suture, are provided. Each resorbable suture desirably, at an opposite end, is moveably coupled to a suture retention hub. FIG. 42 illustrates a section of a patient's stomach wall 99 after four T-bar fasteners 95 are positioned thereon. The "+" in the center of the four T-bar fasteners 95 represents the area where a tissue opening, or stoma, will be made (not shown).

Turning now to the preparation of the safety needle assembly, and as shown generally in FIGS. 8-16 and 39-41, the stylus 50 is inserted into the hollow needle 12 by introducing the blunted distal end 56 of the stylus 50 into the opening 28 at the proximal end 40 of the needle hub 20. The shaft 52 of the stylus 50 is positioned through the opening 28 of the needle hub 20 and through the opening 14 of the shaft 15 of the needle, such that the outer surface 54 of the stylus contacts the inner surface 16 of the needle 12 and a portion of the outer surface 54 of the stylus hub 60 contacts the inner surface 38 of the needle hub 20.

The stylus hub 60 is desirably aligned with the needle hub 20 during this process, so that the retainer, that is, the flanges 68 of the stylus hub 50 and the clips 74 thereon are oriented to align with and move into the upper apertures or upper recesses 30 in the needle hub 20. In such an orientation, the ring or protruding edge 63 on the outer circumference of the upper hub 62 contacts the wedges 47 on the shaft 44 of the handle 42. The wedges 47 act as stops, to prevent the movement of the stylus hub 60 and stylus 50 toward the distal end 18 of the needle 12. Such action is necessary so that the stylus 50 is not inadvertently pushed to move into and through the needle 12, wherein the end 56 of the stylus moves through the distal tip 17 of the needle 12 to blunt the needle assembly 10. Therefore, the handle 42 and wedges 47 thereon cooperate to hold the safety needle assembly 10 in a stable but un-blunted, non-deployed position. If the safety needle assembly is contained within a sheath 80, it is removed therefrom at this time.

Figure 40:
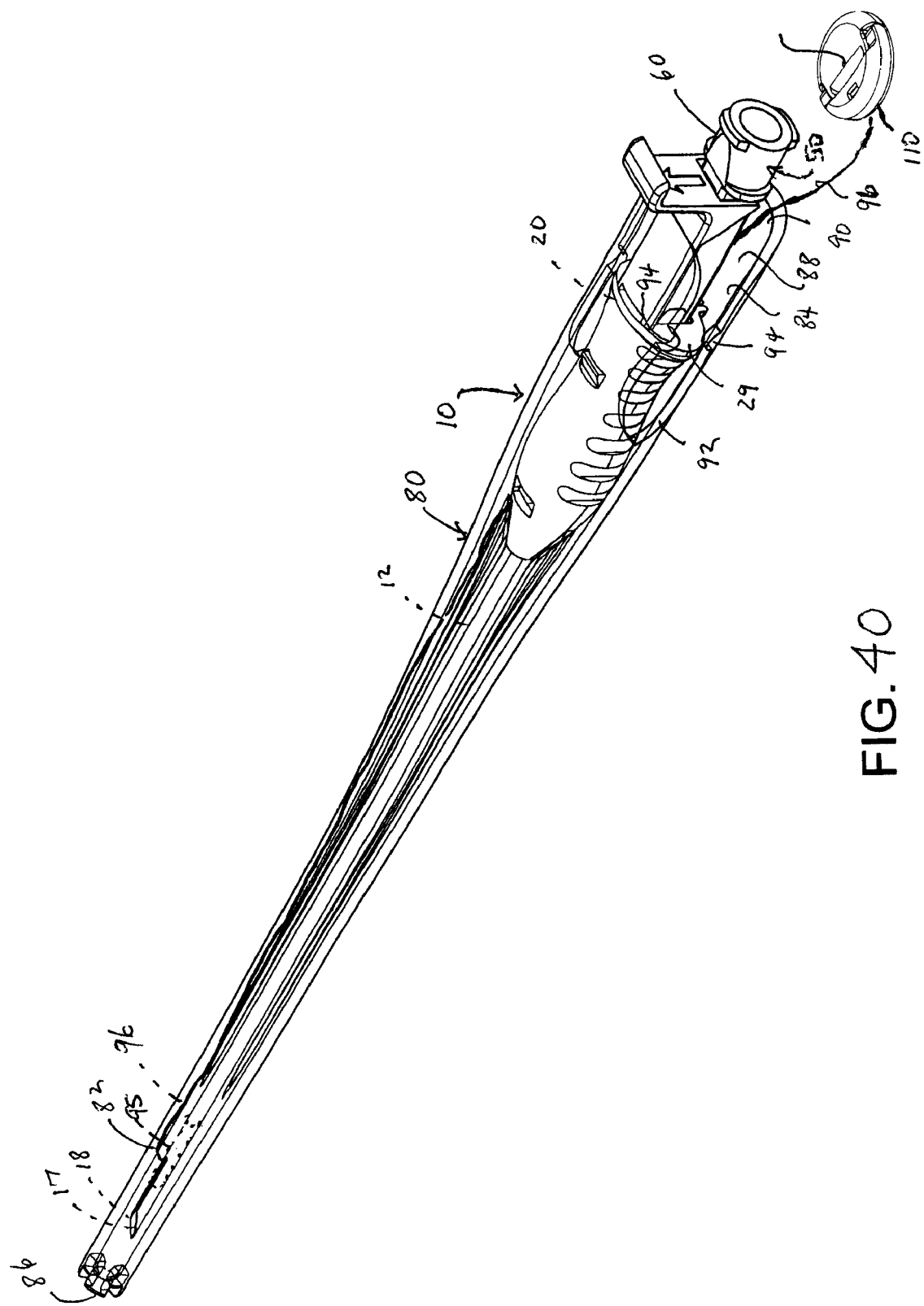
FIG. 40 is a perspective view of the components of the gastropexy kit, including the needle assembly with a fastener positioned thereon (shown in phantom lines), a resorbable suture coupled at one end to the fastener and at the opposite end to the suture retention hub, the needle assembly positioned in the sheath.

It will be appreciated that a substance, such as, for example only, a radio-opaque substance may be loaded into the shaft 15 of the needle 12 prior to, or after, the introduction of the stylus 50 therein. As illustrated in FIGS. 40, 41, 43A and 43B, a fastener 95, for example, a "T-bar" fastener, which is a small cylindrical element which is sized and configured to fit within the distal end 18 and into the shaft 15 of the needle 12 is loaded into the distal end 18 and positioned in the shaft 15. The suture 96 on the fastener 95 is positioned to protrude from the slot 23 in the distal end 18 of the needle 12. The fastener 95 may also be positioned in the shaft 15 of the needle 12 prior to, or after, the introduction of the stylus 50 therein. The "bar" portion of the T-bar fastener 95 is desirably moved proximally in the shaft 15, at least enough so that it does not extend into the opening 14 at the distal end 18 of the needle 12. The remainder of the suture 96 may extend proximally, toward the needle hub 20 and may be releasably held by the hub 20 by passing the suture 96 through a the clip, such as a "C" clip (not shown) on the hub 20. The suture retention hub 110 is desirably positioned on or near an opposite end of the suture 96. Each safety needle assembly is desirably held in a sheath 80 until removed therefrom by a health care provider for use (FIG. 40).

Figure 41:
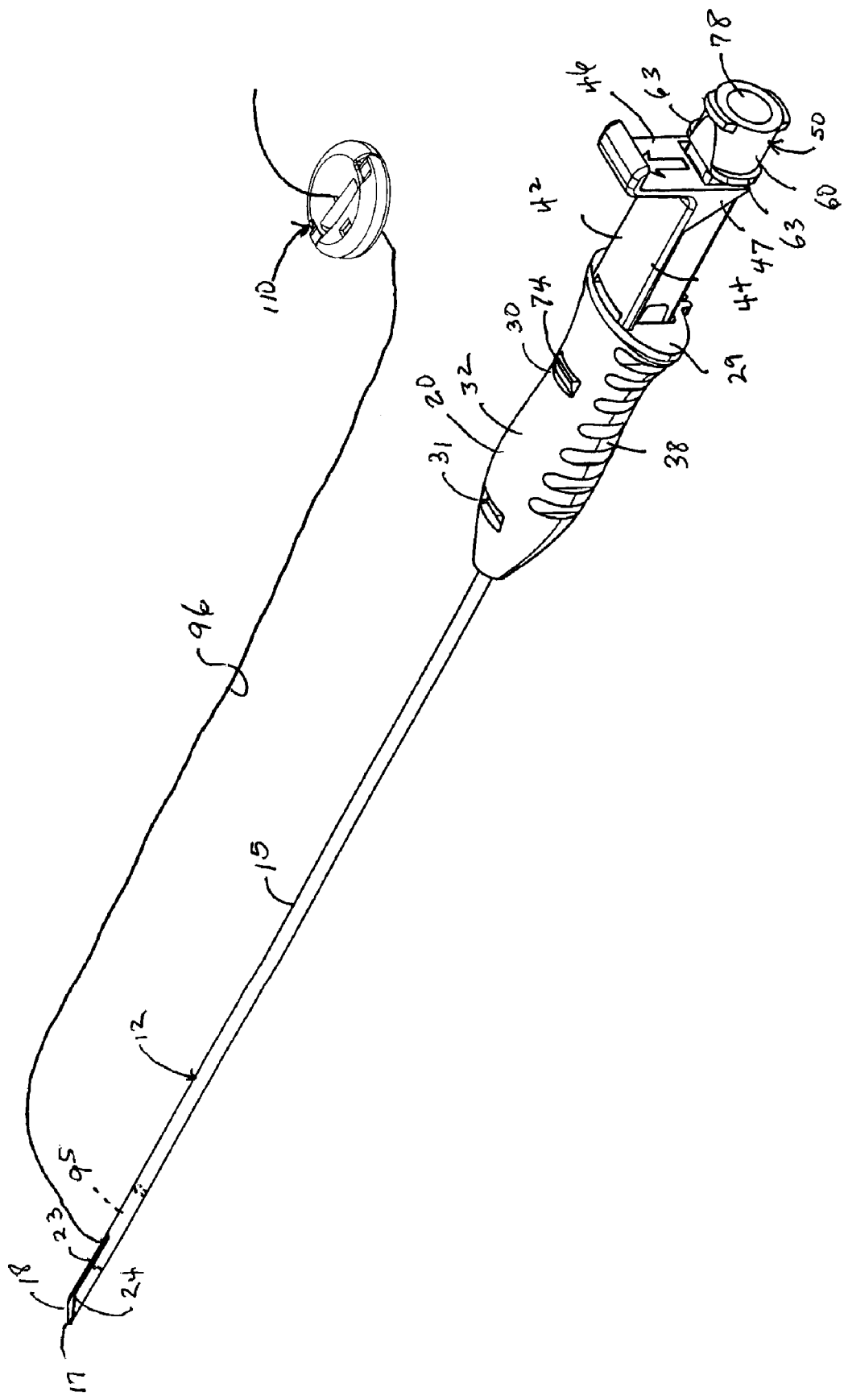
FIG. 41 is a perspective view of the needle assembly with the stylus positioned in the needle and the fastener (shown via phantom lines) positioned near a distal end of the needle, the suture coupled to the fastener extending from the slot in the needle and the suture retention hub coupled to an opposite end of the suture.

The needle assembly 10 is desirably removed from the sheath 80, as shown in FIG. 41, and a health care provider may introduce the needle 12 of the assembly 10 through a patient's skin 97 and abdominal wall into a patient's stomach 98, as shown in FIG. 43A. The stylus 50, after the safety needle assembly 10 has been inserted into the stomach, desirably acts to deploy the T-bar fastener 95 and a portion of the suture 96, into the patient's stomach 98.

Once the needle 12 has been moved to a desired depth so that, for example, the distal end 18 of the needle is positioned in a patient's stomach, the stylus 50 is desirably activated by a health care provider. The provider moves the handle 42 and wedges 47 away from the needle hub 20 by pushing the handle portion 46 downward, thereby positioning the handle 42 in a transverse orientation relative to the needle assembly 10. The handle 42 may desirably, but not by way of limitation, be snapped off and removed from the needle hub 20. The stylus hub 60 is then pushed so that it moves toward the distal end 18 of the needle 12. This action pushes the blunt distal end 56 of the stylus 50 through the shaft 15 of the needle 12 such that the blunt distal end 56 contacts the fastener 95 and pushes or moves it out of the shaft 15 and out of the distal end 18 of the needle 12, as illustrated in FIG. 43B. It will be appreciated that any substance, such as a radio-opaque substance, contained within the shaft 15 of the needle 12 is similarly moved out of the shaft 15 and disposed out with the needle 12 (not shown).

Moving the stylus 50 within the needle 12 acts to position the needle assembly 10 in a blunted position, even while the needle assembly 10 is positioned in a patient's stomach 98. As the stylus 50 is moved toward the distal end 18 of the needle 12, the retainer, namely, the clips 76 on the flanges 68, move out of the upper apertures or upper recesses 30 in the needle hub 20, which act to hold the stylus 50 to the needle 12 and continue in a movement toward the distal end of the needle hub 20 such that the clips 74 move into the lower apertures or lower recesses 31 of the needle hub 20. In this position, the retainer via the clips 76 act to lock the stylus 50 into a non-releaseable locked position relative to the needle 12. Therefore, the safety needle assembly 10 is placed in a stable, blunted position which cannot be altered; the clips 76 cannot be removed from the lower apertures 31 once they are positioned in them. In this blunted position, the safety needle assembly 10 is positioned in a permanently blunted position, and the safety needle assembly 10 is not useable again, and must be disposed of.

Once the fastener 95 has been deployed via the needle assembly 10, the suture retention hub 110 is desirably operated to move the fastener 95 in a position against a wall 99 of a patient's stomach 98 and to move the stomach wall 98 more closely to a patient's skin 97 and to secure it.

In a method of use of the present invention, the suture retention hub 110 is coupled to the suture, desirably a resorbable suture 96. The suture 96 is desirably tensioned so that the fastener 95 is moved closer, and desirably adjacent, the patient's stomach wall 99, as shown in FIG. 44A, by applying tension on the suture 96 until it cannot be pulled further through the opening made by the needle 12. The suture retention hub 110 is desirably positioned such that the second base or handle 114 is positioned transversely at about a 90 degree angle relative to the upper surface 120 of the first base or base 112 of the hub 110, which is desirably positioned in the cover 160 (shown best in FIGS. 36 and 37). In this position, the suture 96 is substantially axially aligned through the various components of the hub 110, and the suture 96 moves freely through the aperture 128 in the bar 124 of the first base or base 112 and through the aperture 146 in the pivot pin 138 of the second base or handle 114, as shown in FIG. 32 and FIG. 44A. This movement allows a health care provider to adjust the hub 110 against the patient's skin 97 and apply tension between the fastener 95 and the hub 110 via the suture 96. Once sufficient tension has been applied, the position of the suture 96 in the hub 110 is locked via the latch assembly of the hub 110. This locked position crimps the suture 96 and prohibits movement of the suture 96 within the hub 110, so that the tension will remain constant. That is, the second base or handle 114 is moved or pivoted so that it is substantially parallel or planar to the upper surface 120 of the base or first base 112, as illustrated in FIG. 31 and FIGS. 44B and C.

To mechanically lock the hub into this position, the second base or handle 114 is pivoted to rest against the flange 136 at the edge 135 of the first base or base 112, and the latch assembly, the knob 158 on the inner edge 156 of the second base or handle 114 is positioned through the opening 137 in the flange 136, thereby positioning the second base or handle 114 in the locked position. In this position, as previously described herein, the suture 96 in the aperture 146 of the pivot pin 138 of the second base or handle 114 is rotated at about a 90 degree angle away from its previous substantially axial alignment with a portion of the suture 96 in the aperture 128 in the bar 124 of the first base 112. This rotation also serves to frictionally crimp or hold the suture 96 between an outer surface 188 of the pivot pin 138 and the inner surface 126 of the bar 124.

The suture 96 may then be knotted on the upper surface 166 of the cover 160, if desired (not shown). In the locked position, the suture 96 in the hub 110 is positioned in a circuitous, crimped "Z" or "S" configuration (FIGS. 31 and 44B).

While it is possible to un-latch the second base or handle 114 from its locked position on the first base or base 112, in many procedures, it would be undesirable to do so. The lip 150 of the upper surface 148 of the second base or handle 114 may be moved upward, thereby moving the knob 158 out of the opening 137 in the flange 136 thereby un-locking the suture 96 in the hub 110. Such a procedure may relax tension on the suture 96, depending upon the angle upon which the second base or handle 114 is positioned.

By using a resorbable suture, which is constructed to dissolve after the critical two to three week period required to stabilize the wall of the stomach and tissue opening or stoma created therein (not shown), no further invasive techniques are required to remove the fastener. When the suture is absorbed, the fastener will move through the patient's digestive tract and be expelled. The suture retention hub will also be released once the suture is absorbed.

The needle 12 is desirably constructed from stainless steel, and may be an 18 gauge thin wall needle. The needle hub 20 is desirably constructed from plastic, and more desirably is a medical grade polycarbonate, medical grade macrolon, or the like. The needle tip may desirably be a non-coring needle tip, and may have a double bevel with reverse grind at the tip. The stylus 50 is desirably also constructed from stainless steel, and may be a 20 gauge thin wall hypodermic tube having a blunted, smooth distal end. The stylus hub 60 is desirably constructed from plastic, and more desirably is a medical grade polycarbonate, medical grade macrolon, or the like. It will be understood, however, that that any portion of the safety needle assembly 10, including the sheath 80, may be constructed from any material or combination of materials, in any gauge or thickness, with any variations, so long as the safety needle assembly 10 operates as shown and/or described herein.

The base 112 of the suture retention hub 110 is desirably constructed from a medical grade polycarbonate. The second base or handle 114 of the hub 110 is desirably constructed from a medical grade polypropylene. The cover 160 of the hub 10 is desirably constructed from a medical grade thermoplastic polyurethane. It will be appreciated, however, that any component of the hub 110 may be constructed from any medically acceptable material(s), so long as the hub 110 operate as shown and/or described herein.

It is desirable that the hub 110 provide a low, flat profile, to increase comfort and decrease the chance of inadvertently hooking the hub 110 on clothing, other devices, and so forth. The height dimension 190 of the hub 110 is desirably in a range of about 0.08 to about 0.140 inches. Even more desirably, the height dimension of the hub 110 is in a range of about 0.09 to about 0.13 inches. Most desirably, the height dimension of the hub 110 is in a range of about 0.100 to about 0.120 inches. When the hub 110 is positioned in the cover, the height dimension is desirably in a range of about 0.150 to about 0.250 inches. Even more desirably, the height dimension of the hub 110 in the cover is about 0.175 to about 0.225 inches. Most desirably, the height dimension of the hub 110 in the cover 160 is about 0.190 to about 0.210 inches.

The hub 110 is desirably wider than its height dimension. Therefore, the hub 110 desirably has a width dimension 192, which includes the cover 160, in a range of about 0.450 to about 0.700. Even more desirably, the width dimension of the hub 110 in the cover 160 is in a range of about 0.048 to about 0.675 inches. Most desirably, the width dimension of the of the hub 110 in the cover 160 is about 0.500 to about 0.650 inches.

The diameter of the aperture 128 through the bar 124 of the first base or base 112, the diameter of the aperture 146 through the pivot pin 138 of the second base or handle 114, the diameter of the aperture 174 and the end diameter of the slit 176 in the cover 160 are each desirably in a range of about 0.024 to about 0.026 inches. More desirably, the diameter of the apertures 128, 146, 174 and end of slit 176 are about 0.025 inches.

It will be appreciated that the first base or base 112 and/or the second base or handle 114 may not include apertures therethrough for the suture (not shown). In this alternative, a suture may extend into an opening in the bar of the base, and may be crimped by the rotation of the pivot pin. In this embodiment, the pivot pin may, but not by way of limitation, contain a bump, knob, and so forth, to create a frictional resistance between the pivot pin and the inner surface of the bar (not shown). In other alternatives, only one opening only through the base 112 may be utilized (not shown). In other alternatives, only one opening through the handle 114 may be utilized (not shown).

The configuration of any component(s) shown or described herein is intended as non-limiting. That is, no component is intended to be limited to a single configuration. Any configuration(s) of any component(s) which permit the component and gastropexy kit to operate as shown and/or described herein may be used.

While the present invention has been described in connection with certain preferred embodiments, it is to be understood that the subject matter encompassed by way of the present invention is not to be limited to those specific embodiments. On the contrary, it will be appreciated that some elements and/or articles may be used with other elements or articles. It is intended for the subject matter of the invention to include all alternatives, modifications and equivalents as can be included within the spirit and scope of the invention.

What is claimed is:

1. A gastropexy kit, comprising:
   a plurality of hollow safety needle assemblies used in the percutaneous fixation of a hollow organ, each safety needle assembly comprising:
   a needle including:
      a needle shaft having a sharp open distal end with a slot therein and an open proximal end, the needle shaft being configured to hold an object in the distal end of the needle, and
      a needle hub at the proximal end of the needle shaft, the needle hub having an opening therethrough which is continuous with an opening provided through the shaft of the needle, the needle hub including at least a first recess and a second recess thereon;
   a stylus including:
      a stylus shaft including a blunt distal end and a proximal end, and
      a stylus hub at the proximal end of the stylus shaft, the stylus hub including at least one retainer which extends a distance away from the stylus such that, when the stylus shaft is positioned inside of the needle shaft, the blunt distal end of the stylus shaft extends a distance toward the open distal end of the needle shaft and, when the stylus hub is positioned inside the needle hub, the retainer is positioned such that at least a portion of the retainer exerts a transverse pressure on an inner surface of the needle hub causing resistance to axial movement of the stylus shaft; and
   a fastener having a suture coupled thereto, the fastener positioned in the distal end of the needle shaft with the suture extending through the slot;
   wherein the stylus shaft is held in a first position when the portion of the retainer is positioned in the first recess of the needle hub such that the blunt distal end of the stylus resists movement toward the open distal end of the needle and is retained within the shaft of the needle, and when the stylus hub is pushed to move the blunt distal end of the stylus through and beyond the sharp open distal end of the needle shaft, the stylus moves within the shaft and contacts the fastener therein thereby ejecting the fastener from the shaft such that the blunt distal end extends beyond the sharp distal end of the needle and the portion of the retainer is positioned in the second recess in the needle hub, thereby rendering the safety needle assembly in a blunted condition, the stylus configured to non-releasably couple to the needle to provide an unmovable position of the stylus with respect to the needle to maintain the blunted condition; and
   a suture retention hub coupled to a portion of each suture, the suture retention hub comprising:
      a base including a bar, the bar having an opening formed therethrough configured to moveably hold a portion of a handle within at least a portion of the base, the base formed to include an aperture therethrough; and
      a handle configured to moveably fit within at least a portion of the base, a portion of the handle having an aperture formed therethough, the portion of the handle positioned within the portion of the base to permit movement of the handle;
      wherein the aperture in the base and the aperture in the handle are substantially in an axial alignment when the handle is positioned transversely relative to an upper surface of the base such that a suture positioned therethrough moves readily through the apertures, and
      wherein the aperture in the base and the aperture in the handle are substantially out of an axial alignment when an upper surface of the handle is positioned in a parallel alignment relative to the upper surface of the base such that a suture positioned therethrough is frictionally crimped in its position in the handle and the base, thereby preventing movement of the suture within the suture retention hub.

2. The gastropexy kit of claim 1, wherein the needle further includes a movable stop at a proximal end of the needle hub, the movable stop comprising a handle having a stop positioned thereon and the stylus further includes a stylus edge at a proximal end of the stylus hub, the stylus edge comprising a protruding rim or ridge.

3. The gastropexy kit of claim 2, wherein when the stop on the handle is positioned against the edge of the stylus, the stylus is held in a position preventing movement toward the distal end of the needle.

4. The gastropexy kit of claim 3, wherein when the handle is moved such that the stop is moved away from the edge of the stylus, the blunt distal end of the stylus shaft is movable to extend through and beyond the sharp open distal end of the needle shaft thereby rendering the safety needle assembly in a blunted condition.

5. The gastropexy kit of claim 2, wherein the handle breaks away from the needle hub.

6. The gastropexy kit of claim 1, wherein the portion of the retainer includes a clip.

7. The gastropexy kit of claim 6, wherein the clip of the retainer is positioned into the first recess of the needle hub to assist the stop in holding the stylus in a non-deployed position.

8. The gastropexy kit of claim 7, wherein when the movable stop is moved away from the portion of the stylus, the blunt distal end of the stylus shaft is movable to extend through and beyond the sharp open distal end of the needle shaft and the retainer is moved such that the clip of the retainer is positioned into the second recess of the needle hub, and the stylus shaft extends through and beyond the distal end of the needle shaft in a deployed position and to render the stylus in an unmoveable position such that the needle assembly is maintained in a safe blunted condition.

9. The gastropexy kit of claim 1, wherein the handle is formed from a resilient material, and the handle resiliently bends to pivotably couple to the base of the hub.

10. The gastropexy kit of claim 1, wherein the suture retention hub includes a cover, and the cover extends at least over the lower surface of the suture retention hub, and is formed of a relatively soft material.

11. The gastropexy kit of claim 1, wherein the width dimension of the suture retention hub is greater than the height dimension of the suture retention hub.

12. The gastropexy kit of claim 1, wherein the suture is resorbable.

13. A gastropexy kit, comprising:
a plurality of hollow safety needle assemblies used in the percutaneous fixation of a hollow organ, each safety needle assembly comprising:
  a needle including:
    a needle shaft having a sharp open distal end having a slot therein and an open proximal end, the needle shaft being configured to hold an object in the distal end of the needle,
    a needle hub at the proximal end of the needle shaft, the needle hub having an opening therethrough which is continuous with an opening provided through the needle shaft, the needle hub including at least a first recess and a second recess therein,
    a movable stop at a proximal end of the needle hub, the movable stop comprising a handle and a stop; and
  a stylus including:
    a stylus shaft including a blunt distal end,
    a stylus hub at the proximal end of the stylus shaft, the stylus hub including at least one retainer which extends a distance away from the stylus shaft, and
    a stylus edge at a proximal end of the stylus hub, the stylus edge comprising a protruding rim or ridge;
  a fastener having a suture coupled thereto, the fastener positioned in the distal end of the needle shaft with the suture extending through the slot;
  wherein the safety needle assembly is configured to move from a non-deployed position in which:
    the stylus hub is positioned inside of the needle hub such that the blunt distal end of the stylus shaft extends a distance toward the open distal end of the needle shaft but is retained within the needle shaft by a portion of the retainer positioned in the first recess in the needle hub, and
    the movable stop is positioned against the stylus edge at the proximal end of the stylus hub and the retainer is positioned such that at least the portion of the retainer exerts a transverse pressure on an inner surface of the needle hub resulting in resistance to axially movement of the stylus,
  to a deployed position in which:
    the movable stop is moved away from the stylus edge, at the proximal end of the stylus hub so that the blunt distal end of the stylus is moved in a distal direction within the needle shaft to contact the fastener and push the fastener out of the shaft, and
    the blunt distal end of the stylus extends through and beyond the sharp open distal end of the needle, and the portion of the retainer is moved to and positioned in the second recess in the needle hub, thereby locking the needle and stylus together in a fixed position and the safety needle assembly is rendered in a blunted condition; and
  a suture retention hub coupled to a portion of each suture, the suture retention hub comprising:
    a first base including an upper surface; and
    a second base moveably coupled to the first base, at least one of the first base and the second base formed to include at least one aperture therethrough;
    wherein when the second base is positioned substantially at a 90 degree angle relative to the upper surface of the first base, a suture positioned through the aperture is moveable through the suture retention hub, and
    wherein when the second base is positioned substantially parallel to the upper surface of the first base, a suture positioned through the aperture is not moveable through the suture retention hub.

14. The gastropexy kit of claim 13, wherein the portion of the retainer includes a clip, and wherein the clip of the retainer is positioned into the first recess of the needle hub to assist the stop in holding the stylus in the non-deployed position.

15. The gastropexy kit of claim 14, wherein when the movable stop is moved away from the portion of the stylus, the blunt distal end of the stylus shaft is movable to extend through and beyond the sharp open distal end of the needle shaft and the retainer is moved such that the clip of the retainer is positioned into the second recess of the needle hub, and the stylus shaft extends through and beyond the distal end of the needle shaft in a deployed position and to render the stylus in an unmovable position such that the needle assembly is maintained in a safe blunted condition.

16. The gastropexy kit of claim 13, wherein the width dimension of the suture retention hub is greater than the height dimension of the suture retention hub.

17. The gastropexy kit of claim 13, wherein the suture positioned in the opening in the first base and the opening in the second base is positioned in a substantially axial alignment in its position in the suture retention hub when the second base is positioned transversely relative to an upper surface of the first base, and the suture moves readily through the suture retention hub when it is in its un-locked position.

18. The gastropexy kit of claim 16, wherein the suture is positioned in the opening in the first base and the opening in the second base is positioned substantially out of axial alignment in its position in the suture retention hub when the second base is positioned about parallel relative to the upper surface of the first base, and the suture is crimped into an unmovable position in the suture retention hub when it is in its locked position.

* * * * *